United States Patent
Bosies et al.

(10) Patent No.: US 6,472,396 B1
(45) Date of Patent: *Oct. 29, 2002

(54) BARBITURIC ACID DERIVATIVES, PROCESSES FOR THEIR PRODUCTION AND PHARMACEUTICAL AGENTS CONTAINING THESE COMPOUNDS

(75) Inventors: Elmar Bosies, Weinheim (DE); Angelika Esswein, Büttelbron (DE); Frank Grams, Mannheim (DE); Hans-Willi Krell, Penzberg (DE); Ernesto Menta, Monza (IT)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/594,700

(22) Filed: Jun. 16, 2000

Related U.S. Application Data

(62) Division of application No. 09/091,352, filed as application No. PCT/EP96/05766 on Dec. 20, 1996, now Pat. No. 6,110,924.

(30) Foreign Application Priority Data

Dec. 23, 1995 (DE) ......................... 195 48 624

(51) Int. Cl.[7] ............... C07D 239/62; C07D 401/04; C07D 403/04; A61K 31/515
(52) U.S. Cl. ................ 514/252.14; 514/270; 544/300; 544/301
(58) Field of Search ............. 514/252.14, 270; 544/123, 243, 299, 300, 301, 302

(56) References Cited

U.S. PATENT DOCUMENTS

| | | | |
|---|---|---|---|
| 2,078,323 A | 4/1937 | Gebauer et al. | 260/33 |
| 2,084,136 A | 6/1937 | Gebauer et al. | 260/33 |
| 3,930,006 A | 12/1975 | Wiggins et al. | 424/254 |

FOREIGN PATENT DOCUMENTS

| | | |
|---|---|---|
| DE | 763145 | 12/1944 |
| DE | 1246743 | 8/1967 |
| WO | 98/58915 | 12/1998 |

OTHER PUBLICATIONS

Skiles, J.W. et al, Ann. Rep. Med. Chem., 35, 2000, p167–176.*
Hagmann, W.K. et al, Ann. Rep. Med. Chem. 31, 1996, p231–240.*
Kappe et al., "Heterocycle syntheses. CIX. Cyclic aminals," Montash. Chem., vol. 99, No. 3, pp. 990–994, 1968.
Goldhahn, "Uber Barbitursaren," Die Pharmazie, vol. 12, No. 9, pp. 549–555, 1957.
Usbeck at al., "Beitrage Zur Analytik Von Kalypnon," Die Pharmazie, vol. 24, pp. 64–68, 1970.
Knabe et al., "Derivatives of Barbituric Acids," Chemical Abstracts, vol. 98, No. 1, Abstract No. 375z, pp. 40, 1983.
Knabe, "On the Enantioselectivity of Drugs," Arz. Forsch., vol. 39, No. 11, pp. 1379–1384, 1989.
Knabe et al., "Derivatives of barbituric acid. XXXII: Central nervous system activity of racemic and optically active barbituric acids with basic substituents," Arch. Pharm., vol. 315, No. 10, pp. 832–839, 1982.
Nagase, "Matrix Metalloproteinases," Zinc Metalloprotease in Health and Disease, Chapter 7, pp. 153–204, 1995.

* cited by examiner

Primary Examiner—Mukund J. Ghan
Assistant Examiner—Thomas C McKenzie
(74) Attorney, Agent, or Firm—Arent Fox Kintner Plotkin & Kahn

(57) ABSTRACT

Compounds of formula I, useful as matrix metalloprotease inhibitors,

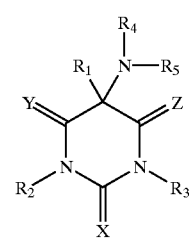

(1)

wherein

X, Y and Z are each oxygen;

$R_1$ is selected from the group consisting of (a) n-octyl, (b) n-decyl, (c) biphenyl and (d) (4-phenoxy)phenyl, wherein the terminal monocycle for moieties (c)–(d) is unsubstituted or substituted by a substituent selected from the group consisting of $-NH_2$, $-NO_2$, $-SO_2NH_2$, $-SO_2CH_3$, acetyl, hydroxy, methoxy, ethoxy, cyano and halogen;

$R_2$ and $R_3$ are each hydrogen; and $R_4$ and $R_5$, together with the nitrogen atom to which they are bound, form a piperazinyl or piperidyl ring, wherein the piperazinyl ring is substituted in the 4-position with a substituent selected from the group consisting of (a) a 6-membered aromatic monocycle having 0, 1 or 2 nitrogen atoms and the remainder of the atoms in the monocycle being carbon and (b) hydroxy-$C_1$–$C_6$ alkyl, wherein the monocycle is unsubstituted or substituted by a substituent selected from the group consisting of halogen, $-NH_2$, $-NO_2$, $-SO_2NH_2$, $-SO_2CH_3$, acetyl and cyano.

7 Claims, No Drawings

BARBITURIC ACID DERIVATIVES, PROCESSES FOR THEIR PRODUCTION AND PHARMACEUTICAL AGENTS CONTAINING THESE COMPOUNDS

This is a divisional of application Ser. No. 09/091,352, filed Jun. 18, 1998, now U.S. Pat. No. 6,110,924, which is a 371 of PCT Application Ser. No. PCT/EP96/05766, filed Dec. 20, 1996.

In normal tissue there is an equilibrium between synthesis and degradation. Extracellular matrix is degraded by proteases which belong to at least three groups of matrix metalloproteases. These are the collagenases, gelatinases and stromelysins. Normally there are specific inhibitors for these catabolic enzymes such as $\alpha_2$ macroglobulines and MMP (=tissue inhibitor of metalloproteases (MMP)) so that an excessive degradation of extracellular matrix does not occur. A related group of proteases is the adamalysins. A prominent member of the adamalysins is TACE (TNF-$\alpha$-converting enzyme).

At least 11 different and yet highly homologous MMP species have been characterized, including the interstitial fibroblast collagenase (MMP-1, HFC), the neutrophil collagenase (MMP-8, HNC), two gelatinases, stromelysins (such as HSL-1) and HPUMP (for a recent review, see Birkedal-Hansen, H., Moore, W. G. I., Bodden, M. K, Windsor, L. J., Birkedal-Hansen; B., DeCarlo, A., Engler, J. A., Critical Rev. Oral Biol. Med. (1993) 4, 197–250. These proteinases share a number of structural and functional features but differ somewhat in their substrate specificity. Only HNC and HFC are capable of cleaving type I, II and III native triple-helical collagens at a single bond with the production of fragments ¾ and ¼ of the native chain length. This lowers the collagen melting point and makes them accessible to further attack by other matrix degrading enzymes.

However, the uncontrolled excessive degradation of this matrix is a characteristic of many pathological states such as e.g. in the clinical picture of rheumatoid arthritis, osteoarthritis, multiple sclerosis, in the formation of tumour metastases, corneal ulceration, inflamative diseases and invasion and in diseases of the bone and teeth.

It can be assumed that the pathogenesis of these clinical pictures can be favourably influenced by the administration of matrix metalloprotease inhibitors. A number of compounds in the meantime are known in the literature (see e.g. the review article of Nigel R A Beeley et al. Curr. Opin. ther. Patents 4 (1), 7 (1994)) or are described in the patent literature, these mainly being peptides with a hydroxamic acid residue, a thiol or phosphine group as a zinc binding group (see e.g. WO-A-9209563 by Glycomed, EP-A-497 192 by Hoffmann-LaRoche, WO-A-9005719 by British Biotechnology, EP-A489 577 by Celltech, EP-A-320 118 by Beecham, U.S. Pat. No. 4,595,700 by Searle among others).

Some of these compounds have a high activity as inhibitors of matrix metalloproteases but only have a very low oral availability.

It has now been found that the claimed new barbituric acid derivatives are very efficacious as matrix metalloprotease inhibitors and have a good oral availability.

The present invention therefore concerns substances of the general formula I

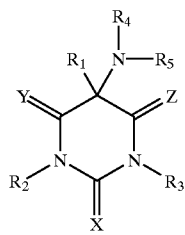

in which

X, Y and Z are independently of one another oxygen, sulphur or NH, $R_1$ represents a group W—V W is a valence dash or a straight-chained or branched $C_1$–$C_8$ alkyl or a $C_2$–$C_8$ alkenyl group which is optionally once or several times substituted, V is an optionally substituted monocycle or bicycle which can contain one or several heteroatoms, or W—V is a C1–C20 akyl group which can be interrupted by heteroatoms, one or several carbon atoms are optionally substituted, $R_2$ and $R_3$ represent hydrogen or one of the two represent lower alkyl or lower acyl $R_4$ and $R_5$ denote independently of each other for A—D wherein A represents a dash alkyl, alkenyl, acyl, alkylsulfonyl, sulfonyl, alkylaminocarbonyl, aminocarbonyl, alkoxycarbonyl, oxy-carbonyl, alkylaminothiocarbonyl, aminothio-carbonyl which is optionally once or several times substituted.

D represents a hydrogen, mono or bicycle, the monocycle or bicycle is optionally once or several times interrupted by heteroatoms and the monocycle or bicycle is once or several times substituted, or $R_4$ and $R_5$ together with the nitrogen atom to which they are bound represent a ring which optionally can be interrupted by a further N atom, said ring can be condensed to a monocycle or bicycle, said ring can optionally be substituted once or several times independently by the residues hydroxy, alkoxy, amino, alkylamino, dialkylamino, nitril or by E—G wherein E represents a dash alkyl, alkenyl, acyl, alkylsulfonyl, sulfonyl, alkylaminocarbonyl, aminocarbonyl, alkoxycarbonyl oxycarbonyl, alkylaminothiocarbonyl, aminothiocarbonyl which is optionally substituted; G represents a hydrogen, mono or bicycle, the monocycle or bicycle is optionally once or several times interrupted by heteroatoms and the monocycle or bicycle is once or several times substituted, pharmacologically acceptable salts or prodrugs thereof as well as the use of these compounds to produce pharmaceutical agents.

The monocycle listed in the case of $R_1$, $R_4$ and $R_5$ is understood as saturated or unsaturated ring systems with 3–8, preferably 5–7 carbon atoms which can optionally be interrupted one or several times by heteroatoms such as nitrogen, oxygen or sulphur in particular a cyclopentyl, cyclohexyl, cycloheptyl, morpholinyl, thiamorpholinyl, piperidinyl, piperazinyl, tetrahydrofuranyl, tetrahydropyranyl, phenyl, pyridyl, pyrimidinyl, pyridazinyl, pyrazinyl, furyl, thiophenyl, imidazolyl, thiazolyl, oxazolyl, isothiazolyl, isoxazolyl, 1,2,3-triazolyl or 1,2,4-triazolyl residue. Lower alkyl, alkoxy and halogen come above all into consideration as substituents.

The bicycle listed under $R_1$, $R_4$ and $R_5$, is understood to be a condensed bicycle or a bicycle of the type monocycle$_1$-L-monocycle$_2$, wherein L denotes a valence dash $C_1$–$C_4$-alkyl group, $C_2$–$C_4$ an alkenyl group, an oxygen or —C(O)— group.

The bicycle is preferably a residue such as a naphthyl, tetrahydronaphthyl dekalinyl, quinolinyl, isoquinolinyl, tetrahydroquino-linyl, tetrahydroisoquinolinyl, indolyl, benzimidazoyl, indazolyl, oxindolyl, benzofuranyl, benzothiophenyl, benzthiazolyl, benzoxazolyl, purinyl, biphenyl or (4-phenoxy)phenyl residue and in particular a naphthyl, biphenyl, quinolinyl, isoquinolinyl, tetrahydroquinolinyl, indolyl or benzimidazolyl residue.

The residues listed under $R_1$, $R_4$ and $R_5$ can optionally be substituted once or several times by halogen, hydroxy, thio, alkyl, hydroxyalkyl, alkoxy, alkylthio, alkylsulfinyl, alkylsulfonyl, amino, alkylamino, dialkylamino, nitro, carboxyl, carboxamido, alkoxycarbonyl, amino or aminocarbonyl optionally substituted once or twice by lower alkyl, nitrile, oxo, thiocarboxamido, alkoxythiocarbonyl, alkmercaptocarbonyl, phosphono, alkylphosphono, dialkylphosphono, alkylsulfonylamido, arylamino, aryl, hetaryl, aryloxy, arylthio, arylsulfinyl, arylsulfonyl or acyl.

In this case the halogen, hydroxy, oxo, thio, alkoxy, alkylthio, amino, aminocarbonyl, carboxyl and acyl groups are preferred.

Lower alkyl denotes $C_1$–$C_6$-Alkyl, preferred methyl, ethyl, propyl, isopropyl or tert.-butyl.

Lower acyl in the residues $R_2$ and $R_3$ above all denotes for —C(O)—$C_1$–$C_6$-alkyl or —C(O)H, preferred for an acetyl group.

The alkyl residues in $R_1$, $R_4$ and $R_5$ can optionally be interrupted once or several time by heteroatoms (O, S, NH).

Alkyl in the residues $R_4$ and $R_5$ denotes as such or in combination with alkoxy, alkylthio, arylsulfonyl, alkylsulfonyl, alkylaminocarbonyl, arylaminocarbonyl, alkylamino, alkoxycarbonyl, aryloxycarbonyl, alkylaminothiocarbonyl, arylaminothiocarbonyl a straight-chained, branched, saturated or unsaturated residue with 1–11, preferably 1–8 carbon atoms such as e.g. a methyl, ethyl, propyl, pentyl, octyl, allyl, propargyl, 2,4-pentadienyl, isopropyl, sec. butyl, 3-methylbutyl, 2-hydroxyhexyl and in particular a methyl, propyl, isopropyl, pentyl, octyl, allyl, 3-methylbutyl, 2-hydroxyhexyl and propargyl residue.

Aryl, also in combination with aryloxy, arylthio, arylsulfonyl, arylaminocarbonyl, aryloxycarbonyl, arylaminothiocarbonyl is understood as a phenyl or naphthyl residue which can optionally be substituted in particular by halogen, lower alkyl or alkoxy.

The $C_1$–$C_{20}$ alkyl group listed for $R_1$ is a straight-chained or branched saturated residue such as e.g. a methyl, ethyl, propyl, butyl, pentyl, octyl, decyl, undecyl, isobutyl, 3-methylbutyl or 7-methyloctyl group. Hydroxy and amino residues come above all into consideration as substituents. The alkyl chains can be interrupted once or several times by oxygen, nitrogen or sulphur. The preferred heteroatom interruption is oxygen (ether linkage) or —C(O)NH— (amid linkage). The most preferred heteroatom interrupted residues are —(CH$_2$CH$_2$O)n—(CH$_2$)mH and n=2 or 3 and m=1 or 2.

W of $R_1$ is preferrably a methyl, ethyl, butyl or hexyl residue; V is in particular a phenyl, Pyridyl, imidazolyl residue which can optionally be substituted above all by lower alkyl, hydroxy, alkoxyamid, sulfonamide or halogen. The most preferred R1 residues are C6–C12-Alkyl residue or a —(CH$_2$)$_n$—C$_6$H$_4$—(CH$_2$)$_m$H residue, wherein m and n are equal or less than 8, the (CH$_2$)-group is optionally interrupted by oxygen, sulfur, or NH and one or two carbons of the phenyl ring are substituted for N-heteroatoms. The alkyl, aryl, hetaryl groups are optionally substituted by small polar substituents.

The most preferred $R_1$ residues are n-Octyl, n-Decyl, Biphenyl or octyl or decyl type residues showing two or three oxygen heteroatoms like 2-(2-(2-methoxyethoxy)ethoxy)ethyl 2-(2-ethoxyethoxy)ethyl or biphenyl-type residues showing one or two nitrogen heteroatoms. The bridging monocycle is optionally ortho substituted and the terminal monocycle of the biphenyl or biphenyl type residue is optionally ortho or para substituted by a small, polar substituent like NH$_2$, —NO$_2$, —SO$_2$NH$_2$, SO$_2$CH$_3$, Acetyl, Hydroxy, Methoxy, Ethoxy or Nitril-group. The para substitution of the terminal monocycle is more preferred.

Halogen is understood as chlorine, bromine, iodine and preferably chlorine.

The hetaryl residues listed for $R_4$ and $R_5$ denote preferred for a pyridine, pyrazine, piperazine, imidazole, thiazole, thiophene or indole ring preferably a pyridine, imidazole and thiophene ring.

The acyl residue listed for the residues $R_4$ and $R_5$ is a residue with 1–10, preferably 6–8 carbon atoms such as e.g. a hexanoyl or octanoyl residue. The alkyl group can be interrupted once or several times by heteroatoms or heteroatom groups like S, O, NH, SO$_2$, amido or carbonyl. These residues can be substituted by amino groups, alkyl groups, aryl groups, arylalkyl groups, alkylamino groups, dialkylamino groups, alkoxy groups and aromatic compounds. These are then amino acid residues preferably a phenylalanine and tryptophan residue in this case.

If $R_4$ and $R_5$ form a ring together with the nitrogen atom to which they are bound, these are 5–7-membered rings preferably a six-membered ring. The piperidine, piperazine, tetrahydroquinoline and tetrahydroiso-quinoline, bicyclo (9.4.0)pentadecyl and 1,2,3,4-tetrahydrobenzo(g) isoquinoline rings are preferred.

If compounds of the general formula I contain one or several asymmetric carbon atoms, the optically active compounds of the general formula I are also a subject matter of the present invention.

Independently of each other the preferred meaning for X, Y, Z is oxygen, for $R_2$ and $R_3$ it is hydrogen. A more preferred combination is X, Y and Z equal each oxygen and $R_2$ is identical to $R_3$ and both mean hydrogen.

It is also preferred that $R_4$ and $R_5$ do not both represent hydrogen.

The term "several" means in connection with heteroatoms in monocycles or bicycles preferred one, two or three more preferred one or two, the most preferred heteroatom is nitrogen.

The term "several" means in connection with substituents or substitution preferred one to five, more preferred one, two or three most preferred one or two.

The term "heteroatom" in connection with alkyl or acyl groups means preferred oxygen or NH, more preferred oxygen.

Substitutions of monocycles or bicycles in $R_1$, $R_4$ and $R_5$ are halogen, nitro, hydroxy, alkoxy, amino, alkylamino, dialkylamino, halogenmethyl, dihalogenmethyl, trihalogenmethyl, phosphono, alkylphosphono, dialkylphosphono, SO$_2$NH$_2$, SO$_2$NH(alkyl), SO$_2$N(alkyl)$_2$, SO$_2$(alkyl), acetyl, formyl, nitril, COOH, COOalkyl, —OC(O)alkyl, —NHC(O)Oalkyl, OC(O)O-aryl, —NHC(S)NH$_2$, —NHC(S)NHalkyl, —NHC(O)-aryl.

The preferred ring structure formed together with the nitrogen $R_4$ and $R_5$, is piperazin or piperidin, both of which are substituted preferrably at the 4-position. In the case of piperidin the 4 position is optionally substituted by a second substitute hydroxy, amino, alkylamino, alkylamino, dialkylamino or alkoxy. The 4 position of piperidin may also form a double bond with the substituent of the 4 position Preferred substitution of the 4 position of piperidin or piperazin are 6-membered aromatic monocycles which are more preferred substituted in para position by small polar substitutions as hydroxy, lower alkoxy, amino, lower alkylamino, lower dialkylamino, nitro, nitrilo, $SO_2NH_2$, $SO_2NH$ lower alkyl, $SO_2$ lower alkyl. The 6 membered aromatic monocycle is preferably bound to the 4 position via a valence bond or a lower alkyl spacer.

In the case that $R_4$ is hydrogen a lower alkyl a lower alkylaryl, then $R_5$ is preferred a acyl derivate preferrably substituted with a monocyle or lower alkylaryl; or a —$CHR_{50}$—$CHR_{51}$—$NR_{52}$—$R_{53}$ wherein $R_{50}$ and $R_{51}$ denote independently of each other for hydrogen, lower alkyl a lower alkoxy. $R_{52}$ denotes for hydrogen or lower alkyl, $R_{53}$ denotes a 6-membered aromatic monocycle which is optionally once or several times substituted and bound to the nitogen preferrably via a valence bond or a lower alkyl spacer.

The most preferred combination of meanings in general formula I are

X equals Y equals Z equals oxygen and $R_2$ equals $R_3$ equals hydrogen and $R_1$ equals n-Octyl, n-Decyl, Biphenyl or octyl or decyl type residues showing two or three oxygen heteroatoms like 2-(2-(2-methoxyethoxy)-ethoxy)ethyl, 2-(2-ethoxyethoxy)ethyl or biphenyl-type residues showing one or two nitrogen heteroatoms; wherein the bridging monocycle is optionally ortho substituted and the terminal monocycle of the biphenyl or biphenyl type residue is optionally ortho or preferred para substituted by a small, polar substituent like $NH_2$, —$NO_2$, —$SO_2NH_2$, $SO_2CH_3$, Acetyl, Hydroxy, Methoxy, Ethoxy or Nitril-group and $R_4$ and $R_5$ form together with the nitrogen to which they are bound a piperazin or piperidin both of which are substituted in the 4 position with a phenyl, pyridyl or pyrazidy ring which is preferred para substituted by a small polar substituent; in the case of piperidin the 4 position may be additionally substituted by hydroxy, lower alkoxy, nitril or amin which may be mono- or disubstituted by lower alkyl.

Compounds of the general formula I can be synthesized by well-known processes preferably in that a) compounds of the general formula II

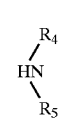

(II)

in which X, Y, Z, $R_1$, $R_2$ and $R_3$ have the above-mentioned meanings and T represents a leaving group such as Hal or $OSO_2R_6$.Hal denoting chlorine, bromine or iodine and $R_6$ denoting an aryl or a methyl residue, are reacted with a compound of the general formula III

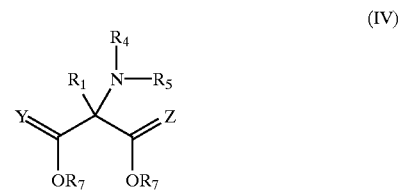

(III)

in which $R_4$ and $R_5$ have the meanings stated above and optionally converted into pharmacologically acceptable salts or b) compounds of the general formula IV

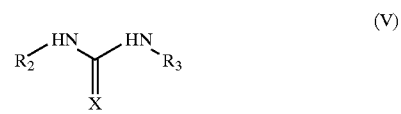

(IV)

in which $R_1$, $R_4$ and $R_5$ have the above-mentioned meanings, Y and Z independently of one another represent oxygen, sulphur or a NH group and $R_7$=methyl, ethyl or phenyl, is reacted with a compound of the general formula V

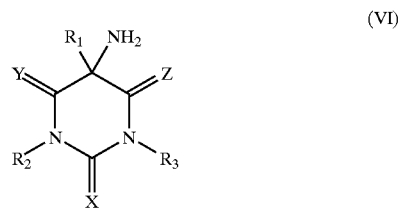

(V)

in which $R_2$, $R_3$ and X have the above-mentioned meanings and optionally converted into pharmacologically acceptable salts or n the case that $R_4$ and/or $R_5$ represent an acyl, alkylsulfonyl, arylsulfonyl, alkylaminocarbonyl, arylaminocarbonyl, alkoxycarbonyl, aryloxycarbonyl, alkylaminothiocarbonyl or arylaminothiocarbonyl residue c) a compound of the general formula VI

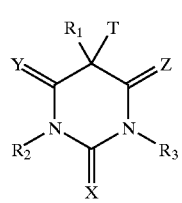

(VI)

in which X, Y, Z, $R_1$, $R_2$ and $R_3$ have the above-mentioned meanings, is reacted with a compound of the general formula VII or VIII $R_8$—D—Hal (VII) $R_8$N=C=A     (VIII)

in which $R_8$ re an optionally substituted alkyl or aryl residue, D=C(O), O—C(O), $SO_2$ or a valency dash, Hal=chlorine, bromine or iodine and A represents oxygen or sulphur and optionally converted into pharmacologically acceptable salts.

Compounds of the general formula II are known in the literature. Thus for example 2,4,6-pyrimidine triones brominated in the 5-position can be synthesized by reacting the appropriate bromomalonic acid diakyl esters with urea (e.g. Acta Chim. Acad. Sci. Hung. 107 (2), 139 (1981)). The corresponding brominated or chlorinated compounds of the general formula II can be obtained by reacting 2,4,6-pyrimidine-triones substituted by $R_1$ in the 5-position with bromine (analogous to J. pr. Chemie 136, 329 (1933) or J. Chem. Soc. 1931, 1870) or sulfuryl chloride (J. Chem. Soc. 1938, 1622). In the same manner one can synthesize the 2-imino-4,6-pyrimidine-diones of the general formula II correspondingly halogenated in the 5-position analogously to Collect. Czech. Comm. 48 (1), 299 (1933). The reaction of 2-thia-4,6-pyrimidine-diones substituted by $R_1$ in the 5-position with bromine in glacial acetic acid (analogous to Am. Chem. J. 34, 186) leads to the compounds of the general formula II correspondingly brominated in the 5-position.

Amines of the general formula III are commercially available or are usually known in the literature.

Compounds of the general formula IV are reacted according to known methods with ureas (see for example J. Med. Chem. 10, 1078 (1967) or Helvetica Chim. Acta 34, 459 (1959) or Pharmacie 38 (1), 65 (1983)), thioureas (see for example Indian J. Chem. 24 (10), 1094 (1985) or J. Het. Chem. 18 (3), 635 (1981)) or guanidines (see for example Collect. Czech. Chem. Comm. 45 (12), 3583 (1980)) of the general formula V.

The reactions are usually carried out in an alcohol such as methanol, ethanol or butanol in the presence of an appropriate sodium alcoholate at temperatures between 40° C. and 100° C. and in the case of the guanidines also at temperatures of up to 200° C. (under pressure). In the case of the thioureas the process is frequently carried out in the presence of acetyl chloride (also as a solvent).

Compounds of the general formula IV are known from the literature or can be produced according to processes known from the literature. They can be synthesized for example by weak acidic hydrolysis of the corresponding bislactim ethers (see J. Chem. Soc. Chem. Comm. 5, 400 (1990)). Other methods of synthesis are for example described in Farmaco Ed. Sci. 31 (7), 478 (1976) or Aust. J. Chem., 23 (6), 1229 (1970).

Ureas, thioureas and guanidines of the general formula V are commercially available.

Compounds of the general formula VI can easily be synthesized by reacting an appropriate substituted acetamidomalonic ester according to process b) and subsequent hydrolytic cleavage of the acetyl group (see Can. J. Chem. 42 (3), 605 (1964)).

Carboxylic acid chlorides of the general formula VII are known or can be synthesized by generally known methods from the corresponding carboxylic acids. The reaction is usually carried out with thionyl chloride or phosphorus tribromide or phosphorus pentabromide or pentachloride in inert solvents such as dichloromethane, diethyl ether, dioxane or tetrahydrofuran at temperatures of 0° C. to 50° C., preferably between 20° C. and 40° C.

Chloroformic acid esters of the general formula VII are known in the literature or can be obtained by generally known methods from the corresponding alcohols by reaction with phosgene or diphosgene. The reaction proceeds in inert solvents such as e.g. diethyl ether, dichloromethane, dioxane, tetrahydrofuran or toluene at temperatures between −20° C. and 20° C. In the case of phosgene the reaction is carried out in the presence of bases, usually tertiary amines such as e.g. triethylamine or pyridine.

Sulfonic acid chlorides of the general formula VII are known or can be synthesized analogously to described methods from the corresponding sulfonic acids by reaction with phosphorus pentachloride or thionyl chloride. The reaction is usually carried out in an inert solvent such as e.g. dimethylformamide or also without a solvent at temperatures of 20° C. to 180° C., preferably at 50° C. to 100° C.

Isocyanates of the general formula VIII are known or can be synthesized by methods known in the literature. Thus for example appropriate alkyl halogenides of the general formula $R_8$—Hal can be reacted with potassium cyanate analogously to Synthesis 1978, 760. Further methods are to react an acid amide of the general formula $R_8$—$CONH_2$ with oxalyl chloride, to thermally decompose an acid azide of the general formula $R_8$—$CON_3$ or to react an amine of the general formula $R_8$—$NH_2$ with phosgene (analogously to Ann. Chem. 562, 110).

Isothiocyanates of the general formula VIII are known in the literature or can be synthesized analogously to known processes. An amine of the genes formula $R_8$—$NH_2$ is preferably allowed to react with carbon disulphide under alkaline conditions analogously to Chem. Ber. 74, 1375.

The reaction of carboxylic acid halogenides, sulfonic acid halogenides or chloroformic acid esters of the general formula VII with amines of the general formula VI is usually carried out in a solvent such as dichloromethane, dimethylformamide or pyridine with addition of an auxiliary base such as triethylamine or 4-diethylaminopyridine at a temperature between −10° C. and 50° C., preferably at room temperature.

Compounds of the general formula I can contain one or several chiral centres and can then be present in a racemic or in an optically active form. The racemates can be separated according to known methods into the enantiomers. Preferably diastereomeric salts which can be separated by crystallization are formed from the racemic mixtures by reaction with an optically active acid such as e.g. D- or L-tartaric acid, mandelic acid, malic acid, lactic acid or camphorsulfonic acid or with an optically active amine such as e.g. D- or L-α-phenyl-ethylamine, ephedrine, quinidine or cinchonidine.

Alkaline salts, earth alkaline salts like Ca or Mg salts, ammonium salts, acetates or hydrochlorides are mainly used as pharmacologically acceptable salts which are produced in the usual manner e.g. by tritrating the compounds with inorganic or organic bases or inorganic acids such as e.g. sodium hydroxide, potassium hydroxide, aqueous ammonia, $C_1$–$C_4$-alkyl-amines such as e.g. triethylamine or hydrochloric acid. The salts are usually purified by reprecipitation from water/acetone.

The new substances of formula I and salts thereof according to the invention can be administered enterally or parenterally in a liquid or solid form. In this connection all the usual forms of administration come into consideration such as for example tablets, capsules, coated tablets, syrups, solutions, suspension etc. Water which contains additives such as stabilizers, solubilizers and buffers that are usual in injection solutions is preferably used as the injection medium.

Such additives are e.g. tartrate and citrate buffer, ethanol complexing agents (such a ethylenediaminetetra-acetic acid and non-toxic salts thereof), high-molecular polymers (such as liquid polyethylene oxide) to regulate viscosity. Liquid carrier substances for injection solutions have to be sterile and are preferably dispensed into ampoules. Solid carrier substances are e.g. starch, lactose, mannitol, methylcellulose, talcum, highly dispersed silicic acids, higher molecular fatty acids (such as stearic acid), gelatins, agar-agar, calcium phosphate, magnesium stearate, animal and vegetable fats, solid high-molecular polymers (such as polyethylene glycols); suitable preparations for oral application can optionally also contain flavourings and sweeteners.

The dosage can depend on various factors such as manner of administration, species, age and/or individual state of health. The doses to be administered daily are about 10–1000 mg/human, preferably 100–500 mg/human and can be taken singly or distributed over several administrations.

Prodrugs of the compounds of the invention are such which are converted in vivo to the pharmacological active compound. The most common prodrugs are carboxylic acid esters.

Within the sense of the present invention the following barbituric acid derivatives are preferred in addition to the compounds mentioned in the examples and compounds that can be derived by combining all meanings of substituents mentioned in the claims:

1. 5-(N-benzyl-N-octyl)-5-phenyl-barbituric acid
2. 5-(N-benzyl-N-phenethyl)-5-phenyl-barbituric acid
3. 5-(N-benzyl-N-[2-(4-pyridyl)ethyl)]-5-phenyl-barbituric acid
4. 5-(N-benzyl-N-[2-(3-pyridyl)ethyl]-5-phenyl-barbituric acid
5. 5-(N-benzyl-N-[2-(2-pyridyl)ethyl]-5-phenyl-barbituric acid
6. 5-(N-benzyl-N-[2-(2-thiophenyl)ethyl]-5-phenyl-barbituric acid
7. 5-[N-(3-methylbutyl)-N-(3-phenylpropyl)]-5-phenyl-barbituric acid
8. 5-(N-benzyl-N-[3-(4-pyridyl)propyl])-5-phenyl-barbituric acid
9. 5-(N-benzyl-N-[2-(2-imidazolyl)ethyl])-5-phenyl-barbituric acid
10. 5-(N-benzyl-N-[2-(1-imidazolyl)ethyl])-5-phenyl-barbituric acid
11. 5-(N-butyl-N-phenylalaninyl)-5-phenyl-barbituric acid
12. 5-(N-butyl-N-tryptophanyl)-5-phenyl-barbituric acid
13. 5-(N-benzyl-N-cyclohexyl)-5-phenyl-barbituric acid
14. 5-[N-benzyl-N-(2-pyridyl)]-5-phenyl-barbituric acid
15. 5-[N-butyl-N-(4-piperidinyl)]-5-phenyl-barbituric acid
16. 5-[N-benzyl-N-2-imidazolyl)]-5-phenyl-barbituric acid
17. 5-(N-octyl-N-phenyl)-5-phenyl-barbituric acid
18. 5-[N-(2-naphthyl)-N-propyl]-5-phenyl-barbituric acid
19. 5-[N-(4-tetrahydroquinolinyl)-N-propyl]-5-phenyl-barbituric acid
20. 5-[N-benzyl-N-(2-thiophenyl)]-5-phenyl-barbituric acid
21. 5-[N-(3-methylbutyl)-N-[3-(4-pyridyl)propyl]]-5-phenyl-barbituric acid
22. 5-[N-(7-methyloctyl)-N-[3-(2-pyridyl)propyl]]-5-phenyl-barbituric acid
23. 5-[N-(2-hydroxyhexyl)-N-[3-(3-pyridyl)propyl])-5-phenyl-barbituric acid
24. 5-(N-benzyl-N-hexanoyl)-5-phenyl-barbituric acid
25. 5-(N-benzyl-N-octanoyl)-5-phenyl-barbituric acid
26. 5-(N-benzyl-N-octanesulfonyl)-5-phenyl-barbituric acid
27. 5-[N-butyl-N-(2-naphthylsulfonyl)]-5-phenyl-barbituric acid
28. 5-(N-hexyloxycarbonyl-N-propyl)-5-phenyl-barbituric acid
29. 5-(N-(4-methoxy-phenylsulfonyl)-N-hexyl]-5-phenyl-barbituric acid
30. 5-[N-(4-butoxy-phenylsulfonyl)]-N-hexyl]-5-phenyl-barbituric acid
31. 5-[N-benzyl-N-(2-phenethyl)]-5-(4-pyridyl)barbituric acid
32. 5-[N-benzyl-N-(2-phenethyl)]-5-(2-pyridyl)barbituric acid
33. 5-(N,N-dipentyl)-5-(4-piperidinyl)barbituric acid
34. 5-(N,N-dioctyl)-5-(2-thiophenyl)barbituric acid
35. 5-(N-benzyl-N-[2-(2-pyridyl)ethyl]-5-(3-imidazolyl)barbituric acid
36. 5-[1-(4-hydroxy)piperidinyl]-5-(4-pyridyl)barbituric acid
37. 5-[1-(4-hydroxy)piperidinyl]-5-(3-pyridyl)barbituric acid
38. 5-[1-(4-hydroxy)piperidinyl]-5-(2-pyridyl)barbituric acid
39. 5-[1-(4-hydroxy)piperidinyl]-5-(4-piperidinyl)barbituric acid
40. 5-[1-(4-hydroxy)piperidinyl]-5-(2-thiophenyl)barbituric acid
41. 5-[1-(4-hydroxy)piperidinyl]-5-(4-imidazolyl)barbituric acid
42. 5-benzyl-5-[1-(4-hydroxy)piperidinyl]barbituric acid
43. 5-[1-(4-hydroxy)piperidinyl]-5-(2-phenethyl)barbituric acid
44. 5-[1-(4-hydroxy)piperidinyl]-5-(1-naphthyl)barbituric acid
45. 5-[1-(4-hydroxy)piperidinyl]-5-(2-naphthyl)barbituric acid
46. 5-(2-quinolinyl)-5-[1-(4-hydroxy)piperidinyl]barbituric acid
47. 5-[1-(4-hydroxy)piperidinyl]-5-(1-isoquinolinyl)barbituric acid
48. 5-[1-(4-hydroxy)piperidinyl]-5-(2-tetrahydroquinolinyl)barbituric acid
49. 5-(2-indolyl-5-[1-(4-hydroxy)piperidinyl]barbituric acid
50. 5-(2-benzimidazolyl)-5-[1-(4-hydroxy)piperidinyl]barbituric acid
51. 5-(1-[4-(2-hydroxyethyl)piperazinyl])-5-octyl-barbituric acid
52. 5-decyl-5-(1-[4-(2-hydroxyethyl)piperazinyl])barbituric acid
53. 5-(1-[4-(2-hydroxyethyl)piperazinyl])-5-undecyl-barbituric acid
54. 5-(1-[4-(2-hydroxyethyl)piperazinyl])-5-(7-methyloctyl)barbituric acid
55. 5-(1-[4-(2-hydroxyethyl)piperazinyl])-5-(8-hydroxyoctyl)barbituric acid
56. 5-(8-aminooctyl)-5-(1-[4-(2-hydroxyethyl)piperazinyl])barbituric acid
57. 5-(1-[4-(2-hydroxyethyl)piperazinyl])-5-(2-phen-ethyl)barbituric acid
58. 5-(1-[4-(2-hydroxyethyl)piperazinyl])-5-(4-phenylbutyl)barbituric acid
59. 5-(1-[4-(2-hydroxyethyl)piperazinyl])-5-(6-phenylhexyl)barbituric acid
60. 5-(1-[4-(2-hydroxyethyl)piperazinyl])-5-[6-(4-methylphenyl)hexyl]barbituric acid
61. 5-(1-[4-(2-hydroxyethyl)piperazinyl])-5-(2-pyridylmethyl)barbituric acid
62. 5-(1-[4-(2-hydroxyethyl)piperazinyl])-5-(4-imidazolylmethyl)barbituric acid
63. 5-(1-[4-(2-hydroxyethyl)piperazinyl])-5-(1-imidazolylmethyl)barbituric acid
64. 5-phenyl-5-(1-(4-propyl)piperazinyl]barbituric acid
65. 5-phenyl-5-(1-tetrahydroquinolinyl)barbituric acid
66. 5-phenyl-5-(1-tetrahydroisoquinolinyl)barbituric acid
67. 5-phenyl-5-[2-(1,2,3,4-tetrahydrobenzo(g)isoquinolinyl]barbituric acid
68. 5-[2-(2-aza-bicyclo[9.4.0]pentadecyl)]-5-phenyl-barbituric acid
69. 5-[2-(2,11-diaza-12-oxo-bicyclo[9.4.0]pentadecyl)]-5-phenyl-barbituric acid 70. 5-(1-[4-(1-oxo-propyl)]piperidinyl)-5-phenyl-barbituric acid
71. 5-[1-(3-oxo-4-propyl)]piperidinyl]-5-phenyl-barbituric acid
72. 5-phenyl-5-[1-(4-propyl)piperazinyl]barbituric acid
73. 5-[1-(3,5-dihydroxy-4-propyl)piperidinyl]-5-phenyl-barbituric acid
74. 5-(4-chlorophenyl)-5-[1-(4-hydroxy)piperidinyl]barbituric acid
75. 5-(4-chlorobenzyl)-5-[1-(4-hydroxy)piperidinyl]barbituric acid
76. 5-[1-(4-hydroxy)piperidinyl]-5-(4-methoxybenzyl)barbituric acid
77. 3-methyl-5-[1-(4-hydroxy)piperidinyl]-5-phenyl-barbituric acid
78. 1-isopropyl-5-[1-(4-hydroxy)piperidinyl]-5-phenyl-barbituric acid
79. 3-acetyl-5-[1-(4-hydroxy)piperidinyl]-5-phenyl-barbituric acid
80. 5-[1-(4-methoxy)piperidinyl]-5-phenyl-2-thio-barbituric acid
81. 2-imino-5-[1-(4-methoxy)piperidinyl]-5-phenyl-barbituric acid
82. 5-[1-(4-methoxy)piperidinyl]-5-phenyl-2,4,6-triimino-barbituric acid
83. 4,6-diimino-5-[1-(4-methoxy)piperidinyl]-5-phenyl-barbituric acid
84. 5-[1-(4-methoxy)piperidinyl]-5-phenyl-2,4,6-trithio-barbituric acid
85. 5-(6-aminohexyl)-5-[N-(2-hydroxyethyl)piperazinyl]barbituric acid
86. 5-(6-formylaminohexyl)-5-[N-(2-hydroxyethyl)piperazinyl]barbituric acid
87. 5-(6-acetylaminohexyl)-5-[N-(2-hydroxyethyl)piperazinyl]barbituric acid
88. 5-[7-ethoxycarbonyl)heptyl]-5-[N-(2-hydroxyethyl)piperazinyl]barbituric acid
89. 5-(8-hydroxyoctyl)-5-[N-(2-hydroxyethyl)piperazinyl]barbituric acid
90. 5-(7-carboxyheptyl)-5-[N-(2-hydroxyethyl)piperazinyl]barbituric acid
91. 5-[(7-aminocarbonyl)heptyl]-5-[N-(2-hydroxyethyl)piperazinyl]barbituric acid
92. 5-[3-((aminocarbonylmethyl)aminocarbonyl)propyl]-5-[N-(2-hydroxyethyl)piperazinyl]barbituric acid
93. 5-[6-(methylamino)hexyl]-5-[N-(4-nitrophenyl)piperazinyl]barbituric acid
94. 5-[4-(n-propyloxy)butyl]-5-[N-(4-nitrophenyl)piperazinyl]barbituric acid
95. 5-[2-(2-(2-methoxyethoxy)ethoxy)ethyl]-5-[N-(4-nitrophenyl)piperazinyl]barbituric acid
96. 5-[2-(2-(ethoxy)ethoxy)ethyl]-5-[N-4-nitrophenyl)piperazinyl]barbituric acid
97. 5-decyl-5-[N-(4-nitrophenyl)piperazinyl]barbituric acid
98. 5-octyl-5-[N-(4-(hydroxysulphonyl)phenyl)piperazinyl]barbituric acid
99. 5-octyl-5-[N-(4-(aminosulphonyl)phenyl)piperazinyl]barbituric acid
100. 5-octyl-5-[N-(4-cyanophenyl)piperazinyl]barbituric acid
101. 5-octyl-5-[N-(4-carboxyphenyl)piperazinyl]barbituric acid
102. 5-octyl-5-[N-(4-(buthoxycarbonyl)phenyl)piperazinyl]barbituric acid
103. 5-octyl-5-[N-(4-(amidino)phenyl)piperazinyl]barbituric acid
104. 5-octyl-5-[N-(4-(aminothiocarbonyl)phenyl)piperazinyl]barbituric acid
105. 5-octyl-5-[N-(4-(methylsulphonyl)phenyl)piperazinyl]barbituric acid
106. 5-octyl-5-[N-(4-(aminocarbonyl)phenyl)piperazinyl]barbituric acid
107. 5-octyl-5-[N-(4-(methylcarbonyl)phenyl)piperazinyl]barbituric acid
108. 5-octyl-5-[N-(4-(dimethylphosphonyl)phenyl)piperazinyl]barbituric acid
109. 5-octyl-5-[N-(4-(amino)phenyl)piperazinyl]barbituric acid
110. 5-octyl-5-[N-(4-acetylamino)phenyl)piperazinyl]barbituric acid
111. 5-octyl-5-[N-(4-trifluoroacetylamino)phenyl)piperazinyl]barbituric acid
112. 5-octyl-5-[N-(4-(methylsulphonylamino)phenyl)piperazinyl]barbituric acid
113. 5-octyl-5-[N-(5-nitropyrid-2-yl)piperazinyl]barbituric acid
114. 5-octyl-5-[N-(N-oxypyrid-4-yl)piperazinyl]barbituric acid
115. 5-octyl-5-[N-(4-(5-triazolyl)phenyl)piperazinyl]barbituric acid
116. 5-octyl-5-[(N-benzoyl-N-benzyl)amino]barbituric acid
117. 5-[4-(phenyl)phenyl]-5-[(N-benzoyl-N-benzyl)amino]barbituric acid
118. 5-(4-[4-Nitrophenyl)piperazinyl])-5-octyl-barbituric acid
119. N-Benzyl-3-(4-nitro-phenyl)-N-(2,4,6-trioxo-5-phenyl-hexahydro-pyrimidin-5-yl)-acrylamide
120. N-Benzyl-2-(3-bromo-phenyl)-N-(2,4,6-trioxo-5-phenyl-hexahydro-pyrimidin-5-yl)-acetamide

EXAMPLE 1

5-(1-[4-(2-Hydroxyethyl)piperazinyl])-5-phenyl-barbituric Acid

5-Bromo-5-phenyl barbituric acid (Acta Chim. Acad. Sci. Hung. 107 139–45 (1981)) (7 mmol) and N-(2-hydroxyethyl)-piperazine (8 mmol) are suspended in 40 ml absolute ethanol. After 3 hours under reflux it is concentrated in a vacuum. The residue is purified by chromatography on silica gel (ethyl acetate/methanol 3:1). Colourless crystals are obtained by recrystallization from isopropanol. Yield 56%; Fp. 238–40° C. (decomp.).

EXAMPLE 2

5-(1-[4-(4-Methylphenyl)methyl]piperazinyl]-5-phenyl-barbituric Acid

5-Bromo-5-phenyl-barbituric acid (7 mmol) and N-(methyl-p-tolyl)-piperazin (8 mmol) are suspended in 40 ml absolute ethanol. After 2 hours under reflux it is concentrated in a vacuum. The residue is triturated with diethy ether, sucked off, rewashed with 20 ml diethyl ether and dried. The crude product is purified by chromatography on silica gel (acetone). One obtains colourless crystals. Yield 72%; Fp. 247–48° C.

EXAMPLE 3

5-(1-[4-(4-Methylphenyl))butylpiperazinyl])-5-phenyl-barbituric Acid 4-(p-Tolyl)-butyl Bromide The compound is prepared analogously to the literature. Synth. Commun. 22(20)2945-8 (1992). Yield 91% colourless oil.

Phenyl-(4-(p-tolyl)-butyl)-malonic Acid Diethyl Ester

Phenylmalonic acid diethyl ester (8.8 mmol) dissolved in 5 ml absolute tetrahydrofuran is added dropwise to 20 ml absolute tetrahydrofuran and sodium hydride (9.7 mmol). Then 4-p-tolylbutyl bromide (8.8 mmol) dissolved in 10 ml absolute tetrahydrofuran is added after 15 minutes. It is heated for 3 days under reflux. The solvent is concentrated in a vacuum. The residue is taken up in 50 ml ethyl acetate and extracted with 2×50 ml water. The organic phase is dried over magnesium sulfate, filtered and concentrated by evaporation. It is purified by chromatography on silica gel (heptane/ethyl acetate 9:1). Yield 55% colourless oil.

5-1-[4-(4-(4-Methylphenyl))butyl]piperazinyl)-5-phenyl-barbituric Acid

Urea (4.6 mmol) and phenyl-4-(p-tolyl)-butyl)-malonic acid diethyl ester (3.1 mmol) are added to a solution of sodium ethylate (6.2 mmol) in absolute ethanol. It is heated for 12 hours under reflux, then concentrated in a vacuum and the residue is taken up in 15 ml water. The mixture is adjusted to pH 1–2 with 6 N hydrochloric acid and extracted with 2×30 ml ethyl acetate. The organic phase is dried over magnesium sulfate, filtered and concentrated by evaporation. The residue is purified by chromatography on silica gel (heptane/ethyl acetate 3:1). Yield 46% colourless crystals; Fp. 163–5° C.

EXAMPLE 4

5-(1-[4-(2-Hydroxyethyl)piperazinyl])-5-phenyl-barbituric Acid 14.6 g (50 mmol) phenylmalonic acid diethyl ester and subsequently 10 g (166 mmol) urea are slowly added to 1.3 g sodium in 40 ml methanol while stirring. It is heated for 2 hours while slightly boiling. In this process a precipitate forms. It is cooled to 10–15° C., subsequently slowly admixed with 12.9 g (100 mmol) 4-(2-hydroxyethyl) piperidine, 13.8 g (100 mmol) potassium carbonate and 2.87 ml (112.3 mmol) bromine. The mixture is stirred for 2 hours at 10–15° C., then slowly heated to boiling and boiled for 1 hour under reflux. After cooling it is poured onto 240 ml 1n nitric acid, the solution is washed once with toluene and neutralized with a saturated sodium acetate solution. A greasy mass precipitates which is taken up in hot ethanol. The hot solution is treated with active carbon and admixed with warm water until turbidity starts. After cooling the crystals are suction filtered. Yield: 7.3 g=44%; Fp.: 222–223° C.

EXAMPLE 5

5-Phenyl-5-(1-piperidinyl)barbituric Acid

5-Phenyl-5-(1-piperidinyl)barbituric acid in a yield of 92%; Fp.: 244–246° C. is obtained analogously to example 4 using piperidine instead of 4-(2-hydroxyethyl)piperidine.

EXAMPLE 6

5-[1-(4-Hydroxy)piperidinyl-5-phenyl-barbituric Acid

5-[1-(4-Hydroxy)piperidinyl-5-phenyl-barbituric acid in a yield of 39%; Fp.: 241–242° C. (from ethanol) is obtained analogously to example 4 using 4-hydroxy-piperidine instead of 4-)2-hydroxyethyl)piperidine.

EXAMPLE 7

5-[1-(4,4-Dimethyl)piperidinyl]-5-phenyl-barbituric Acid

5-[1-(4,4-Dimethyl)piperidinyl]-5-phenyl-barbituric acid in a yield of 69%; Fp.: 238–240° C. (from ethanol/water) is obtained analogously to example 4 using 4,4-dimethyl-piperidine instead of 4-(2-hydroxyethyl)piperidine.

EXAMPLE 8

5-[1-(4-Methyl)-piperidinyl]-5-phenyl-barbituric Acid

5-[1-(4-Methyl)piperidinyl]-5-phenyl-barbituric acid in a yield of 87%; Fp.: 208–209° C. (from methanol/water) is obtained analogously to example 4 using 4-methyl-piperidine instead of 4-(2-hydroxyethyl)piperidine.

EXAMPLE 9

5-[1-(4-Methoxy)piperidinyl]-5-phenyl-barbituric Acid

5-[1-(4-Methoxy)piperidinyl]-5-phenyl-barbituric acid in a yield of 67%; Fp.: 184–185° C. (from ethanol/water) is obtained analogously to example 4 using 4-methoxy-piperidine instead of 4-(2-hydroxyethyl)piperidine.

EXAMPLE 10

5-Ethyl-5-[1-(4-methyl)piperidinyl]barbituric Acid 14.1 g (75 mmol) ethylmalonic acid diethyl ester and subsequently 15 g (264 mmol) urea is slowly added to 1.95 g sodium in 60 ml methanol while stirring. After boiling for 2 hours a precipitate forms. It is cooled to 10–15° C. and sucessively slowly admixed with 15 g (15 mmol) 4-methylpiperidine, 21 g (150 mmol) potassium carbonate and 4.3 ml 168 mmol) bromine. The mixture is stirred for 2 hours at this temperature, slowly heated to boiling and heated for 1 hour under reflex. After cooling it is poured onto 360 ml 1 N nitric acid, the solution is washed once with toluene and admixed with an excess of saturated sodium acetate solution. The precipitated precipitate is recrystallized from ethanol with addition of active carbon. Yield: 4.4 g=23%; Fp.: 194–195° C.

EXAMPLE 11

5-Ethyl-5-[1-(4-methoxy)piperidinyl]barbituric Acid

5-Ethyl-5-[1-(4-methoxy)piperidinyl]barbituric acid in a yield of 15%; Fp.: 201–202° C. (from ethanol) is obtained analogously to example 10 using 4-methoxypiperidine instead of 4-methylpiperidine.

EXAMPLE 12

5-Ethyl-5-(1-(4-hydroxy)piperidinyl]barbituric Acid

5-Ethyl-5-(1-(4-hydroxy)piperidinyl]barbituric acid in a yield of 5%; Fp.: 110–112° C. (from ethanol) is obtained analogously to example 10 when using 4-hydroxypiperidine instead of 4-methoxypiperidine.

EXAMPLE 13

5-Ethyl-5-[1-(4-(2-hydroxyethyl)piperidinyl] barbituric Acid

5-Ethyl-5-[1-(4-(2-hydroxyethyl)piperidinyl]barbituric acid in a yield of 17%; Fp.: 238–240° C. (from methanol) is obtained analogously to example 10 using 4-(2-hydroxyethyl)piperidine instead of 4-methylpiperidine.

EXAMPLE 14

5-(4-Methoxyphenyl)-5-[N-(2-hydroxyethyl)piperazinyl]barbituric Acid a) Preparation of Ethyl 4-Methoxyphenylacetate A solution of 4-Methoxyphenylacetic acid (2 g) and para-toluenesulfonic acid (230 mg) in 30 ml of ethanol is refluxed for 2 hours. The solvent is evaporated under reduced pressure and the residue is suspended in a saturated aqueous solution of sodium hydrogencarbonate and extracted twice with ethyl acetate. The organic extracts are collected, washed with water and dried over sodium sulfate to give, after evaporation of the solvent under reduced pressure, 2.14 g of the product.

b) Preparation of Ethyl 4-Methoxyphenyl malonate

A mixture of ethyl 4-Methoxyphenylacetate (27.8 g) and sodium (3.68 g) in 90 ml of diethylcarbonate is refluxed for 3 hours, then the solvent is evaporated under reduced pressure and the residue is diluted with water and neutralized with acetic acid. The aqueous phase is extracted twice with diethyl ether. The organic extracts are pooled and washed twice with 1 N sodium hydroxide and once with water, then the organic phase is dried over sodium sulfate and concentrated to dryness. 34.2 g of the product are obtained.

c) Preparation of 5-(4-Methoxyphenyl)barbituric Acid

To a solution of 660 mg of sodium in 50 ml of ethanol are added 3.86 g of ethyl 4-Methoxyphenyl malonate and 1.28 g of urea. The reaction mixture is refluxed for 3 hours. A white solid separates, which is collected by filtration and redissolved in 15 ml of water. The solution is acidified to pH=1–2 by adding 6 N hydrochloric acid. A white solid separates, which is filtered and washed on the filter with water. After drying under vacuum at 50° C. for several hours, 2.28 g of the product are obtained.

d) Preparation of 5-Bromo-5-(4-Methoxyphenyl)barbituric Acid

To a suspension of 5-(4-Methoxyphenyl)barbituric acid (222 mg) in 3 ml of water, cooled to 0–5° C. with ice bath, are added 136 µl of 48% hydrobromic acid and 56 µl of bromine, dropwise. After 1 hour at a temperature below 10° C., the solid which separated is collected by filtration and washed on the filter with water. The solid is dried for several hours under vacuum at 50° C., to give 283 mg of the product.

e) Preparation of the Title Compound

A solution of 5-Bromo-5-(4-Methoxyphenyl)barbituric acid (11.5 g) and N-(2-hydroxyethyl)piperazine (15.755 g) in 260 ml of methanol is refluxed for about 2 hours, then the solid which separated is collected by filtration, redissolved in 100 ml of methanol and heated at reflux for 1 hour. The solid is filtered again and dried at 80° C. under vacuum to give 9 g of the product containing 8–9% of methanol. The solid is dissolved in 40 ml of 1 N hydrochloric acid, then the solution is basified with 3.42 g of sodium hydrogencarbonate and cooled at 0–5° C. for 4 hours. The product is recovered by filtration and it is dried under vacuum at 80° C. for several hours, to give 8.55 g of the pure product, m.p. 247–248° C.

$^1$H-NMR in d6-DMSO: 2.36 ppm (m, 6H); 2.55 ppm (m, 4H); 3.44 ppm (q, 2H); 3.74 ppm (s, 3H): 4.33 ppm (t, 1H); 6.95 ppm (d, 2H); 7.3 ppm (d, 2H); 11.54 ppm (br s, 2H).

EXAMPLE 15

5-[3-(4-Methoxyphenyl)propyl]-5-[4-(2-hydroxyethyl)piperazinyl]barbituric Acid a) Preparation of 3-(4-Methoxyphenyl)propionyl Chloride To a suspension of 3-(4-Methoxyphenyl)propionic acid (10 g) in 150 ml of toluene are added 8 ml of thionyl chloride and the mixture is heated to 65° C. for 4 hours. The solvent is evaporated off under reduced pressure and the residue is redissolved in toluene and concentrated to dryness. Such steo is repeated twice. 11 g of the product are obtained as a yellow oil.

b) Preparation of 5-[3-(4-Methoxyphenyl)propionyl]barbituric Acid

To a suspension of barbituric Acid (6.4 g) in 48 ml of pyridine are added dropwise 11 g of 3-(4-Methoxyphenyl)propionyl chloride and the mixture is stirred at room temperature for 18 hours. The reaction mixture is then poured into ice and acidified to pH=1 by adding 6 N hydrochloric acid. A solid precipitates, which is filtered and resuspended in methanol. The suspension is kept under stirring for 15 minutes, then the solid is recovered by filtration to give 12.2 g of the product m.p. 248–250° C.

c) Preparation of 5-[3-(4-Methoxyphenyl)propyl]barbituric Acid

To a suspension of 10 g of 5-[3-(4-Methoxyphenyl)propionyl]barbituric Acid in 100 ml of acetic acid are added portionwise 4.5 g of sodium cyanoborohydride, then the mixture is heated to 60° C. After 1 hour the reaction mixture is cooled to room temperature and poured into ice. After 30 minutes a solid is recovered by filtration, which is dried under vacuum at 50° C. to give 8.74 g of the product, m.p. 195–197° C.

d) Preparation of 5-Bromo-5-[3-(4-Methoxyphenyl)propyl]barbituric Acid

A mixture of 5-[3-(4-Methoxyphenyl)propyl]barbituric Acid (2.5 g), N-bromosuccinimide (2 g) and dibenzoyl peroxide (catalytic amount) in 110 ml of carbon tetrachloride is refluxed for about 1 hour, then the solid which separated is filtered. The solid is redissolved in ethyl acetate and filtered through a silica gel cake in order to eliminate the succinimide residue. The organic phase is then concentrated to dryness and the residue is crystallized from diethylether/carbon tetrachloride mixture. A pale yellow solid separates which is filtered and dried under vacuum at 60° C. to give 2.8 g of the product, m.p. 113–114° C.

e) Preparation of the Title Compound

A of 5-Bromo-5-[3-(4-Methoxyphenyl)propyl]barbituric Acid (710 mg) and N-(2-hydroxyethyl)piperazine (281 mg) in 25 ml of ethanol is refluxed for 4 hours. The solvent is evaporated under reduced pressure and the residue is partitioned between 1 N hydrochloric acid and ethyl acetate. The aqueous phase is basified to pH=6–7 and extracted with ethyl acetate. The organic phase is concentrated to dryness and the residue is crystallized from ethyl acetate to give 30 mg of the product.

$^1$H-NMR in d6-DMSO: 1.32 ppm (m, 2H); 1.86 ppm (m, 2H); 2.33 ppm (m, 6H); 2.45 ppm (m, 2H); 2.53 ppm (m, 4H); 3.43 ppm (q, 2H); 3.7 ppm (s, 3H); 4.35 ppm (t, 1H); 6.8 ppm (d, 2H); 7.04 ppm (d, 2H); 11.53 ppm (br s, 2H).

EXAMPLE 16

5-Phenyl-5-[4-(2-hydroxyethylidene)piperidinyl]barbituric Acid a) Preparation of 4-(Ethoxycarbonylmethylidene)Piperidine To a suspension of sodium hydride (2.6 g) in 30 ml of tetrahydrofuran, cooled to 0° C. and kept under nitrogen atmosphere, 13 ml of triethylphosphonoacetate, dissolved in 10 ml of tetrahydrofuran are added dropwise. The temperature is then brought to room temperature and the stirring is continued for 30 minutes. The mixture is again cooled to 0° C. and it is added dropwise with a solution obtained by adding portionwise to a solution of 4-piperidone monohydrate hydrochloride (10 g) in THF 2.6 g of sodium hydride, filtered to eliminate the sodium chloride which formed. At the end of the addition, the temperature is brought to room temperature and the stirring is continued for 20 hours. The solvent is then evaporated under reduced pressure and the residue is redissolved in ethyl acetate and washed with 1 N hydrochloric acid. The aqueous phase is extracted with ethyl acetate and chloroform, then it is basified to pH=9–10 by adding 20% sodium hydroxide and it is extractedb with chloroform. The aqueous phase is then salted and extracted again with chloroform three times. The pooled extracts are dried over sodium sulfate and evaporated to give 7.1 g of the product as a yellow oil.

b) Preparation of 4-(Hydroxyethylidene)Piperidine

A solution of 15 ml of DIBAL (1.5 M solution in toluene) in 20 ml of toluene is added dropwise with 0.976 g of 4-(ethoxycarbonylmethylidene)piperidine, dissolved in few milliliter of toluene. The reaction mixture is stirred at room temperature for 2 hours, then it is cooled to 0–5° C. and added dropwise with methanol, until the gaz development is seen. The mixture is concentrated to a little volume and diethyl ether is added: a white solid separates, which is filtered off. The organic phase is concentrated to dryness, redissolved in diethyl ether and again filtered. The clear solution is concentrated to dryness to give 500 mg of the product.

c) Preparation of the Title Compound

A mixture of 5-Bromo-5-phenylbarbituric Acid (2.45 g), 4-(hydroxyethylidene)piperidine (1.053 g) and triethylamine (1.15 ml) in 50 ml of ethanol is refluxed for 2 hours. The solvent is evaporated under reduced pressure and the residue is purified by silica gel chromatography (40 g; eluent: ethyl acetate/petroleum ether 8:2), to give 450 mg of the product.

$^1$H-NMR in d6-DMSO: 2.13 ppm (m, 4H), 2.55 ppm (m, 4H); 3.89 ppm (d, 2H); 4.46 ppm (br s, 1H); 5.24 ppm (t, 1H); 7.42 ppm (m, 5H); 11.6 ppm (br s, 2H).

50 mg of 5-phenyl-5-[4-(2-hydroxyethyl)-1,2,5,6-tetrahydropyridinyl]barbituric Acid as a side product are also recovered.

$^1$H-NMR in d6-DMSO: 1.96 ppm (m, 2H); 2.09 ppm (t, 2H); 2.64 ppm (t, 2H); 3.00 ppm (m, 2H); 3.47 ppm (q, 2H); 4.43 ppm (t, 1H); 5.3 ppm (m, 1H); 7.4 ppm (s, 5H); 11.63 ppm (br s, 2H).

EXAMPLE 17

5-Phenyl-5-[N-(2-hydroxyethyl)piperazinyl]-2-thiobarbituric Acid a) Preparation of Diethyl 2-Bromo-2-phenylmalonate To a solution of diethyl 2-phenylmalonate (15 ml) in 200 ml of tetrahydrofuran, kept at 0° C. and under nitrogen atmosphere, 3.475 g of sodium hydride are added and the mixture is kept 30 minutes under stirring at 0° C., then it is brought to room temperature. After cooling again to 0° C., the reaction mixture is added with 14.3 g of N-bromosuccinimide. After about 15 minutes, the white solid which separated is filtered off and the filtrate is concentrated to dryness to give a residue which is redissolved in chloroform and dried over sodium sulfate. The solvent is evaporated under reduced pressure to give 15.66 g of the product.

b) Preparation of Diethyl 2-phenyl-2-[4-(2-hydroxyethylpiperazinyl]malonate

A solution of diethyl 2-Bromo-2-phenylmalonate (16.8 g) in 150 ml of dimethylsulfoxide is heated to 90–100° C., then N-(2-hydroxyethyl)piperazine (27.9 g) is added and the reaction mixture is heated for additional 4 hours. The mixture is poured into water and extracted with ethyl acetate three times. The pooled organic extracts are washed with 1 N hydrochloric acid. The aqueous phase is basified with 1 N sodium hydroxide to pH=8–9 and it is extracted twice with ethyl acetate. The organic extracts are collected and are washed with a saturated aqueous solution of sodium chloride and dried over sodium sulfate. After removal of the solvent under reduced pressure, the residue is crystallized from diethylether/petroleum ether 1:1 to give 6.5 g of the product, m.p. 63–64° C.

c) Preparation of the Title Compound

To a solution of sodium (27 mg) in 3 ml of ethanol are added 218 mg of diethyl 2-phenyl-2-[4-(2-hydroxyethyl)piperazinyl]malonate and 288 mg of thiourea, then the mixture is refluxed for about 13 hours. The reaction mixture is cooled to room temperature and 140 μl of acetic acid are added, then the solvent is evaporated under reduced pressure. The residue is redissolved in a ethyl acetate/methanol 9:1 mixture. The solid which separates is filtered off and the filtrate is concentrated to dryness and purified by silica gel chromatography (eluent: from ethyl acetate to ethyl acetate/methanol 9:1), to give, after crystallization from ethyl acetate, 30 mg of the product, m.p. >250° C.

$^1$H-NMR in d6-DMSO: 2.4 ppm (m, 6H); 2.59 ppm (m, 4H); 3.46 ppm (q, 2H); 4.4 ppm (t, 1H); 7.4 ppm (m, 5H), 12.5 ppm (br s, 2H).

EXAMPLE 18

5-Phenyl-5-[N-(2-hydroxyethyl)piperazinyl-2-azobarbituric Acid

To a solution of sodium (70 mg) in 5 ml of ethanol are added 218 mg of diethyl 2-phenyl-2-[4-(2-hydroxyethyl)piperazinyl]malonate (example 4- step b) and 172 mg guanidine hydrochloride and the mixture is refluxed for 8 hours. Further 57 mg of guanidine hydrochloride are added and the mixture is refluxed for additional 6 hours. The temperature is brought to room temperature and acetic acid is added until neutralization occurs, then the solid which is formed is filtered off. The filtrate is concentrated to dryness and redissolved in ethanol, from which by adding of ethyl acetate a solid separates. After 1 hour at −4° C. the white solid is recovered by filtration and it is recrystallized from methanol (2 ml), to give, after drying under vacuum at 90° C. for 4 hours, 78 mg of the product, m.p. >250° C.

$^1$H-NMR in d6-DMSO: 2.33 ppm (m, 6H); 2.54 ppm (m, 4H); 3.41 ppm (t, 2H); 4.33 ppm (br s, 1H); 7.00 ppm (br s, 1H); 7.33 ppm (m, 5H); 7.5 ppm (br s, 1H); 11.4 ppm (br s, 1H).

EXAMPLE 19

5-Benzyl-5-[N-(2-hydroxyethyl)piperazinyl] barbituric Acid a) Preparation of 5-benzylidenebarbituric A suspension of 5 g of barbituric Acid in 50 ml of water is heated until a compklete dissolution occurs, then it is added with 4.3 ml of benzaldheide. The mixture is refluxed for 1 hour, then the solid which separated is filtered, washed several times with water and dried under vacuum at 100° C. to give 8.17 g of the product, m.p. >258° C.

b) Preparation of 5-Benzylbarbituric Acid

To a suspension of 5-benzylidenebarbituric Acid (4 g) in 200 ml of methanol are added portionwise 1.4 g of sodium borohydride. After 10 minutes from the end of the addition, 100 ml of water are added and the mixture is acidified with 1 N hydrochloric acid to pH=2. The solvent is evaporated off and the aqueous phase is extracted with ethyl acetate. The pooled extracts are dried over sodium sulfate and concentrated to dryness. 3.6 g of the product crystallize, m.p. 207–209° C.

c) Preparation of 5-Bromo-5-benzylbarbituric Acid

To a suspension of 5-benzylbarbituric Acid (1.7 g) in 15 ml of water, cooled to 0–5° C. 1 ml of 48% hydrobromic acid are added followed by the addition dropwise of 0.437 ml of bromine into the reaction mixture. After 1 hour under stirring at a temperature below 10° C. the solid which formed is separated by filtration and washed with water. 2.17 g of the product are obtained, m.p. 164–166° C.

d) Preparation of the Title Compound

A solution of 5-Bromo-5-benzylbarbituric Acid (2.15 g) and N-(2-hydroxyethyl)piperazine in 50 ml of ethanol is refluxed for 4 hours, then it is cooled to room temperature and added with 4 ml of triethylamine. The solvent is evaporated off and the white residue is redissolved in a ethyl acetate/methanol 3:1 mixture. An ornage solid crystallizes, which is recovered by filtration. After recrystallization from ethanol 0.62 g of the product are obtained, m.p. 243–246° C.

$^1$H-NMR in d6-DMSO: 2.43 ppm (t, 2H); 2.58 ppm (m, 4H); 3.03 ppm (m, 4H); 3.34 ppm (s, 2H); 3.49 ppm (q, 2H); 4.5 ppm (t, 1H); 7.13 ppm (m, 5H); 8.8 ppm (br s, 2H).

EXAMPLE 20

5-[N-(2-Hydroxyethyl)piperazinyl]-5-(4-hydroxyphenyl)barbituric Acid a) Preparation of 5-(4-Hydroxyphenyl)barbituric Acid To a suspension of 5-(4-Methoxyphenyl)barbituric Acid (222 mg) in 5 ml of methylene chloride, kept at −5/−10° C. and under nitrogen atmosphere, is dropped a solution of boron tribromide (473 μl) in 2 ml of methylene chloride. The stirring is continued for additional 2 hours at −5° C., then the temperature is brought to room temperature and stirring is continued for further 20 hours. The reaction mixture is again cooled to 0° C. with an ice bath and it is basified to pH=9–10 by adding dropwise 5% sodium hydroxide. The aqueous phase is separated, filtered through a celite plug, cooled with ice bath and acidified to pH=1 with 37% hydrochloric acid. A white solid separates which after 1 hour is separated by filtration and dried under vacuum at 60° C. to give 215 mg of the product.

b) Preparation of 5-[4-(Tertbutyldimethylsilyloxy)phenyl]barbituric Acid

To a solution of 5-(4-hydroxyphenyl)barbituric Acid (1.9 g) and tertbutyl dimethylsilyl chloride (4.68 g) in 20 ml of anhydrous dimethylformamide are added 4.4 g of imidazole and the mixture is heated to 55° C. for 5 hours. The temperature is then brought to room temperature and the reaction mixture is poured into 1 N hydrochloric acid and extracted twice with ethyl acetate. The pooled organic extracts are washed with water and dried over sodium sulfate. By concentration of the solution a white solid separates, which is kept at 0° C. overnight, then it is filtered to give 2.185 g of the product.

c) Preparation of 5-Bromo-5-[(4-tertbutyldimethylsilyloxyphenyl]barbituric Acid

To a suspension of 5-[4-(tertbutyldimethylsilyloxy)phenyl]barbituric Acid (330 mg) and dibenzoyl peroxide (catalytic amount) in 10 ml of carbon tetrachloride are added 210 mg of N-bromosuccinimide. The mixture is stirred at room temperature for 1 hour, then the solvent is evaporated off and the residue is purified by silica gel chromatography (eluent: petroleum ether/ethyl acetate 8:2), to give 260 mg of the product.

d) Preparation of 5-(N-(2-Hydroxyethyl)piperazinyl]-5-[(4-tertbutyldimethylsilyloxy)phenyl]barbituric Acid A solution of 5-Bromo-5-[(4-tertbutyldimethylsilyloxy)phenyl]barbituric Acid (260 mg) and N-(2-hydroxyethyl)piperazine (98 mg) in 5 ml of ethanol is refluxed for 1 hour, then it is brought to room temperature and added with 0.3 ml of triethylamine. The solvent is evaporated off and the residue is purified by silica gel chromatography (25 g; eluent: ethyl acetate/methanol 3:1), to give, after crystallization from ethyl acetate, 170 mg of the product, m.p. 220–221° C.

e) Preparation of the Title Compound

A mixture of 5-[N-(2-hydroxyethylpiperazinyl]-5-[(4-tertbutyldimethylsilyloxy)phenyl]barbituric Acid (148 mg), tetrabutylammonium fluoride (1.1 M in THF; 0.6 ml) and acetic acid (290 μl) in 10 ml of tetrahydrofuran, kept at 0° C., is stirred for 2 hours 30 minutes, then the solvent is evaporated off and the residue is purified by silica gel chromatography (12 g; eluent: ethyl acetate/methanol 3:1), to give, after crystallization from ethyl acetate and recrystallization from ethyl acetate/methanol mixture. 40 mg of the product, m.p. >25° C.

$^1$H-NMR in d6-DMSO: 2.37 ppm (m, 6H); 2.55 ppm (m, 4H); 3.45 ppm (q, 2H); 4.35 ppm (t, 1H); 6.76 ppm (d, 2H); 7.17 ppm (d, 2H); 9.72 ppm (s, 1H); 11.47 ppm (br s, 2H).

EXAMPLE 21

5-[N-(2-hydroxyethylpiperazinyl]-5-(3-hydroxyphenyl)barbituric Acid a) Preparation of Ethyl 3-Hydroxyphenylacetate A suspension of 3-hydroxyphenylacetic acid (5.4 g) and para-toluensulfonic acid (650 mg) in 80 ml of ethanol is refluxed for 4 hours, then the solvent is evaporated off and the residue is dissolved in ethyl acetate and washed twice with a saturated aqueous solution of sodium hydrogencarbonate. The organic phase is dried over sodium sulfate and the solvent is evaporated off to give 6.08 g of the product as a yellow oil.

b) Preparation of Ethyl 3-(Tertbutyldimethylsilyloxy)phenylacetate

To a solution of ethyl 3-hydroxyphenylacetate (6 g) and tertbutyldimethylsilyl chloride (6 g) in 80 ml of anhydrous dimethylformamide are added 5.66 g of imidazole and the mixture is stirred at room temperature for 1 hour 30 minutes. The reaction mixture is then poured into water and extracted twice with ethyl acetate. The pooled organic extracts are dried over sodium sulfate and concentrated to dryness to give 10 g of the product as a yellow oil.

c) Preparation of Diethyl 3-(Tertbutyldimethylsilyloxyphenylmalonate

To a solution of ethyl 3-(tertbutyldimethylsilyloxy)phenylacetate (10 g) in 25 ml of diethylcarbonate are added portionwise 0.86 g of sodium and the mixture is refluxed for 2 hours. The solvent is evaporated off and the residue is poured into water (90 ml). The pH is adjusted to pH=6 with acetic acid and the mixture is extracted with diethyl ether. The organic phase is dried over sodium sulfate and concentrated to dryness to give 10 g of an orange oil which is purified by silica gel chromatography (eluent: petroleum ether/ethyl acetate 95:5), to give 2.45 of the product.

d) Preparation of 5-[3-Tertbutyldimethylsilyloxy)phenyl]barbituric Acid

To a solution of diethyl 3-(tertbutyldimethylsilyoxy)phenylmalonate (1.5 g) in 15 ml of ethanol are added 0.445 g of sodium ethoxide and 0.295 g of urea and the mixture is refluxed for 3 hours. The reaction mixture is cooled to room temperature and the solid formed is filtered. The solid is redissolved in water, the pH is adjusted to pH=1–2 with 6 N hydrochloric acid and the soild which precipitates is recovered by filtration. The filtrate is concentrated to eliminate the ethanol, then the solution is basified and extracted with ethyl acetate. The organic phase is concentrated to dryness to give 250 mg of residue which is pooled with the solid previously filtered (350 mg). The residue so obtained contains a mixture of the product along with the de-silylated derivative.

Such a residue (550 mg) is dissolved in 5 ml of anhydrous dimethylformamide and 790 mg of tertbutyldimethylsilyl chloride and 745 mg of imidazole are successively added. The mixture is heated to 55° C. for 5 hours. Further 75 mg of imidazole and 79 mg of tertbutyldimethylsilyl chloride are added and the heating is continued for an additional hour. The reaction mixture is then poured into 1 N hydrochloric acid and extracted three times with ethyl acetate. The pooled organic extracts are washed with water and dried over sodium sulfate. The solution is concentrated and a white solid precipitates. 710 mg of the product are recovered by filtration.

e) Preparation of 5-[3-(Tertbutyldimethylsilyloxy)phenyl]-5-bromobarbituric Acid A mixture of 5-[3-(tertbutyldimethylsilyloxy)phenyl] barbituric Acid (680 mg), N-bromosuccinimide (432 mg) and dibenzoyl peroxide (catalytic amount) in 10 ml of carbon tetrachloride are stirred at room temperature for 1 hour. The solvent is evaporated off and the residue is purified by silica gel chromatography (eluent:ethyl acetate/hexane 7:3) to give 550 mg of the product, m.p. 170–172° C.

f) Preparation of 5-[N-(2-Hydroxyethyl)piperazinyl]-5-[3-(tertbutyldimethylsilyloxy)phenyl]barbituric Acid A solution of 5-[3-(tertbutyldimethylsilyloxy)phenyl]-5-bromobarbituric Acid (444 mg) and N-(2-hydroxyethyl) piperazine (420 mg) in 10 ml of methanol is stirred at room temperature for 5 hours, then the solvent is evaporated off and the residue is purified by silica gel chromatography (13 g, eluent:ethyl acetate/methanol 3:1), to give 70 mg of the product.

g) Preparation of the Title Compound

To a solution of 5-[N-(2-hydroxyethyl)piperazinyl]-5-[3-(tertbutyldimethylsilyloxy)phenyl]barbituric Acid (170 mg) in 12 ml of tetrahydrofuran, kept at 0° C. and under nitrogen atmosphere, are added 333 µl of acetic acid and 0.69 ml of tetrabutylammonium fluoride. The mixture is stirred for 3 hours then the solvent is evaporated off and the residue is purified by silica gel chromatography (15 g; eluent:ethyl acetate/methanol 4:1), to give, after crystallization from methanol, 35 mg of the product, m.p. 219–221° C.

$^1$H-NMR in d6-DMSO: 2.37 ppm (m, 6H); 2.59 ppm (m, 4H); 3.45 ppm (q, 2H); 4.35 ppm (t, 1H); 6.74 ppm (m, 2H); 6.92 ppm (t, 1H); 7.18 ppm (t, 1H); 9.62 ppm (s, 1H); 11.54 ppm (br s, 2H).

EXAMPLE 22

5-[N-(2-hydroxyethyl)piperazinyl]-5-(4-Methylphenyl)barbituric Acid a) Preparation of 5-(4-Methylphenyl)barbituric Acid To a solution of sodium (184 mg) in 12 ml of ethanol are added 0.95 ml of diethyl 2-(4-Methylphenyl)malonate and 360 mg of urea, then the mixture is refluxed for 3 hours. A white solid separates, which is filtered and redissolved in 4 ml of water. The solution is acidified to pH=1–2 by adding 6 N hydrochloric acid. A white solid separates, which is collected by filtration, washed with 15 ml of water and dried under vacuum. 619 mg of the product are obtained, m.p. 271° C.

b) Preparation of 5-Bromo-5-(4-Methylphenyl)barbituric Acid

To a suspension of 5-(4-Methylphenyl)barbituric Acid (218 mg) in 2 ml of water, kept at 10° C. under stirring, 136 µl of 48% hydrobromic acid are added then 56 µl of brominr are dropped and the stirring is continued for 3 hours. The precipitate which formed is recovered by filtration and washed with water, then it is dried under vacuum to give 270 mg of the product, m.p. 210–213° C.

c) Preparation of the Title Compound

A solution of 5-Bromo-5-(4-Methylphenyl)barbituric Acid (3.1 g) and of N-(2-hydroxyethyl)piperazine (1.53 g) in 60 ml of ethanol is refluxed for 3 hours. The solvent is evaporated off and the residue is dissolved in 1 N hydrochloric acid and washed twice with ethyl acetate. The aqueous phase is basified with 1 N sodium hydroxide and extracted with ethyl acetate. The organic extracts are concentrated to dryness and the residue is purified by silica gel chromatography (100 g; eluent:ethyl acetate/methanol 3:1), to give, after evaporation of the solvent, 1.97 g of the product as hydrobromide.

The free base is obtained by treating an ethyl acetate suspension (200 ml) of the salt with 50 ml of a saturated aqueous solution of sodium hydrogencarbonate and by extraction of the aqueous phase with ethyl acetate. By concentrating to dryness the pooled organic extracts 1.18 g of the product are obtained.

$^1$H-NMR in d6-DMSO: 2.3 ppm (s, 3H), 2.35 ppm (m, 6H); 2.57 ppm (m, 4H); 3.45 ppm (q, 2H), 4.35 ppm (t, 1H); 7.19 ppm (d, 2H); 7.28 ppm (d, 2H); 11.55 ppm (br s, 2H).

EXAMPLE 23

5-Octyl-5-[N-(2-hydroxyethyl)piperazinyl]barbituric Acid a) Preparation of Diethyl 2-Octylmalonate To a solution of 2.63 of sodium in 100 ml of ethanol is added dropwise a solution of 19.1 ml of diethylmalonate in 10 ml of ethanol. The mixture is successively added with 20.4 ml of 1-bromooctane dissolved in 10 ml of ethanol, then the mixture is refluxed for 6 hours. The reaction mixture is concentrated to a little volume and the residue is partitioned between a saturated aqueous solution of sodium hydrogenphosphate (200 ml) and ethyl acetate (200 ml). The organic phase is washed with 75 ml of water and 75 ml of saturated aqueous solution of sodium chloride, dried over sodium sulfate and concentrated to dryness, to give 31.8 g of the product as an oil.

$^1$H-NMR in CDCl$_3$: 0.80–0.95 ppm (m, 3H), 1.15–1.40 ppm (m, 18H); 1.88 ppm (q, 2H); 3.33 ppm (t, 1H), 4.19 ppm (q, 4H).

b) Preparation of 5-Octylbarbituric Acid

To a solution of sodium (5.32 g) in 400 ml of anhydrous ethanol is added a solution of diethyl 2-octylmalonate (31.5 g) in 50 ml of ethanol and successively 10.27 g of urea, then the mixture is refluxed for 2 hours 30 minutes. The mixture is rapidly cooled to room temperature and the solid which was formed is recovered by filtration and washed with diethyl ether. The solid is then dissolved in 200 ml of water and acidified with 6 N hydrochloric acid until pH 1.5–2 is reached. A solid separates. The mixture is added with 200 ml of ethyl acetate and it is stirred for 2 hours, then it is added with additional 800 ml of warm ethyl acetate. The organic phase is separated and the aqueous phase is washed with 200 ml of ethyl acetate. The pooled organic phases are washed with 250 ml of saturated aqueous solution of sodium chloride dried over sodium sulfate and concentrated to dryness. 21.03 g of the product are obtained.

$^1$H-NMR in d6-DMSO: 0.77–0.80 ppm (m, 3H); 1.23 ppm (s, 12H); 1.80–1.95 ppm (m, 2H); 3.52 ppm (t, 1H); 11.15 ppm (s, 2H).

c) Preparation of 5-Bromo-5-Octylbarbituric Acid

To a suspension of 5-octylbarbituric Acid (20 g) in 120 ml of water, cooled at 0–5° C., are added 12 ml of 48% hydrobromic acid and successively are dropped 4.72 ml of bromine. Ater 2 hours under stirring, the white solid which separated is recovered by filtration, washed with water and partitioned between 200 ml of diethyl ether and 100 ml of water. The aqueous phase is extracted with additional 50 ml of diethyl ether. The pooled organic phases are washed with 75 ml of saturated aqueous solution of sodium chloride, dried over sodium sulfate and concentrated to dryness. 25.8 g of the product as white solid are obtained.

$^1$H-NMR in d6-DMSO: 0.78–0.90 ppm (m, 3H); 1.10–1.38 ppm (m, 12H), 2.20–2.34 ppm (m, 2H), 11.80 ppm (s, 2H).

d) Preparation of the Title Compound

To a solution of 5-Bromo-5-octylbarbituric Acid (23.52 g) in 70 ml of dimethylsulfoxide, kept under nitrogen atmosphere and at a temperature of 5–10° C., is dropped N-(2-hydroxyethyl)piperazine (36.2 g), then the mixture is stirred at room temperature for 2 hours 30 minutes. The reaction mixture is poured into water (1 l) under stirring and cooling with an ice bath. The white solid which separates is recovered by filtration, washed with water and dried under vacuum at 40° C. to give, after crystallization from ethanol (140 ml) 10.91 g of the product as a white solid, m.p. 183–184° C.

$^1$H-NMR in d6-DMSO: 0.75–0.88 ppm (m, 3H); 0.90–1.10 ppm (m, 2H); 1.12–1.30 ppm (m, 10H); 1.75–1.90 ppm (m, 2H); 2.23–2.40 ppm (m, 6H); 2.45–2.60 ppm (m, 4H); 3.45 ppm (br t, 2H); 4.35 ppm (br s, 1H); 11.55 ppm (s, 2H).

EXAMPLE 24

5-naphtyl-5-[N-(2-hydroxyethyl)piperazinyl] barbituric Acid a) Preparation of Ethyl 2-Naphtylacetate To a solution of 2-naphtylacetic acid (5 g) in 50 ml of ethanol are added 0.5 g of paratoluensulfonic acid, then the reaction mixture is refluxed for about 4 hours. The solvent is evaporated off and the residue is dissolved in diethyl ether, washed twice with a saturated aqueous solution of sodium hydrogencarbonate and once with brine, then the pooled organic extracts are dried over sodium sulfate and concentrated to dryness. 5.64 g of the product as a yellow oil are obtained.

b) Preparation of Diethyl 2-Naphtylmalonate

To a solution of ethyl 2-naphtylacetate (2 g) in 23.3 ml of diethylcarbonate, kept under stirring and at room temperature, are added portionwise 0.232 g of sodium. The reaction mixture is refluxed for 2 hours 30 minutes, then it is concentrated in order to eliminate the not reacted diethylcarbonate and it is added with 20 ml of cold water. The resulting mixture is acidified with acetic acid until weak acidity is reached, then it is extracted three times with diethyl ether. The pooled organic extracts are dried over sodium sulfate and the solvent is evaporated off, to give, after recrystallization from diethyl ether (19 ml), 1.015 g of the product as a white solid.

c) Preparation of 5-Naphtylbarbituric Acid

A solution of sodium (0.32 g) in 30 ml of anhydrous ethanol is added with diethyl 2-naphtylmalonate (2 g) and successively with urea (0.63 g). The mixture is refluxed for 2 hours, then the solid which separated is recovered by filtration, then it is dissolved in 7 ml of water and acidified to pH=1 with 6 N hydrochloric acid. A white solid precipitates which, after 30 minutes under stirring, is filtered and washed with water. The solid is dried overnight under vacuum at 40° C., to give 0.96 g of the product.

d) Preparation of 5-Bromo-5-Naphtylbarbituric Acid

A suspension of 5-naphtylbarbituric Acid (0.2 g) in 1.5 ml of 95% ethanol, cooled at 0° C. and kept under stirring, is added dropwise with 48% hydrobromic acid (0.5 ml) and successively with 4.4 μl of bromine. After 4 hours under stirring at room temperature the solid is filtered and washed with water, then it is dried under vacuum at 40° C. overnight. 0.25 g of the product are obtained.

e) Preparation of the Title Compound

To a suspension of 5-Bromo-5-naphtylbarbituric Acid (0.24 g) in 3.5 ml of ethanol is added a solution of N-(2-hydroxyethyl)piperazione (0.112 g) in 1.5 ml of ethanol. The reaction mixture is refluxed for 5 hours, then it is cooled to room temperature and the solid which separates is filtered off. The filtrate is added with 100 μl of triethylamine, then the solvent is evaporated off to give 0.364 g of a solid, which is recrystallized from a mixture of methanol (4.5 ml) and ethyl acetate (10 ml). The obtained solid (70 mg) is washed under stirring with an ethyl acetate/water mixture for 2 hours and dried under vacuum at 40° C. for 8 hours, to give 60 mg of the product.

$^1$H-NMR in d6-DMSO: 2.3–2.5 ppm (m, 6H); 2.6 ppm (m, 4H); 3.45 ppm (m, 2H); 4.35 ppm (t, 1H); 7.4–8.1 ppm (m, 7H); 11.65 ppm (s, 2H).

EXAMPLE 25

5-(4'-Biphenyl)-5-[N-(2-hydroxyethyl)piperazinyl] barbituric Acid a) Preparation of Ethyl (4'-Biphenyl)acetate A suspension of (4'-biphenyl)acetate acid (6.4 g) in 60 ml of ethanol is added with 1.1 g of para-toluensulfonic acid, then the reaction mixture is refluxed for 4 hours 30 minutes. The solvent is evaporated off, the residue is dissolved in diethyl ether and the resulting organic phase is washed three times with a saturated aqueous solution of sodium hydrogencarbonate and once with brine. The organic phase is then dried over sodium sulfate and the solvent is evaporated off to give 7.1 g of the product as a yellow oil.

b) Preparation of Diethyl (4'-Biphenyl)malonate

A solution of ethyl (4'-biphenyl)acetate (7.1 g) in 60 ml of diethylcarbonate, kept under nitrogen atmosphere, is added portionwise with sodium (0.734 g), then it is heated at 120° C. for 3 hours. The solvent is evaporated off and the residue is dissolved in 65 ml of cold water and acidified with acetic acid until pH=5–6 is reached. The aqueous phase is then extracted three times with diethyl ether and the pooled organic extracts are dried over sodium sulfate and concentrated to dryness. The residue is purified by silica gel chromatography (eluent:petroleum ether/diethyl ether 9.4:0.6) to give 7.05 g of the product, m.p. 51–53° C.

c) Preparation of 5-(4'-Biphenyl)barbituric Acid

A solution of sodium (0.322 g) in 40 ml of anhydrous ethanol is added with diethyl (4'-biphenyl)malonate (2.2 g) and successively with urea (0.63 g. The reaction mixture is refluxed for 3 hours 30 minutes, then it is cooled to room temperature and the solid is recovered by filtration. The obtained solid is redissolved in 40 ml of warm water and the resulting aqueous phase is acidified to pH=1 with 6 N hydrochloric acid. The solid which separates is kept 15 minutes under stirring, then it is filtered and dried under vacuum at 60° C. 1.1 g of the product are obtained, m.p. >240° C.

d) Preparation of 5-Bromo-5-(4'-biphenyl)barbituric Acid

A suspension of 5-(4'-biphenyl)barbituric Acid (0.28 g) in 1.4 ml of water, cooled at 0° C. and kept under stirring, is added dropwise with 0.14 ml of 48% hydrobromic acid and successively with 55.5 µl of bromine. The temperature is then brought to room temperature and the stirring is continiued for 1 hour. The suspended solid is recovered by filtration, washed with water and dried under vacuum at 60° C. for 2 hours, to give 0.336 of the product, m.p. 203–205° C.

e) Preparation of the Title Compound

To a suspension of 5-Bromo-5-(4-biphenyl)barbituric Acid (0.323 g) in 4.4 ml of ethanol 0.14 g of N-(2-hydroxyethyl)piperazine are added and the reaction mixture is refluxed for 2 hours. The upended solid is filtered off and the resulting clear solution is treated with 125 µl of triethylamine, then the solvent is evaporated off. The residue is redissolved in 2 ml of ethanol, from which crystallizes a solid which is stirred for 30 minutes, then it is filtered. The residue is recrystallized from ethanol to give 100 mg of the pure product, m.p. 225–226° C.

$^1$H-NMR in d6-DMSO: 2.3–2.5 ppm (m, 6H); 2.65 ppm (m, 4H); 3.45 ppm (m, 2H); 4.4 ppm (s, 1H); 7.3–7.8 ppm (m, 9H); 11.6 ppm (s, 2H).

EXAMPLE 26

5-(4'-Biphenyl)-5-[N-(4-nitrophenyl)piperazinyl]barbituric Acid

A solution of 5-Bromo-5-(4'-biphenyl)barbituric Acid (0.359 g; example 25, step d) in 9 ml of methanol is added with 0.622 g of N-(4-nitrophenyl)piperazine and the mixture is refluxed for about 2 hours. The solvent is evaporated off and the residue is partitioned between water and ethyl acetate. The organic phase is separated, washed with brine and dried over sodium sulfate. The solvent is then evaporated under reduced pressure to give 0.74 g of a residue which is purified by silica gel chromatography (eluent:methylene chloride/acetone 9:1) to give 400 mg of the product, m.p. 181° C.

$^1$H-NMR in d6-DMSO: 2.8 ppm (m, 4H); 3.5 ppm (m, 4H); 7.00 ppm (d, 2H); 7.3–7.85 ppm (m, 9H); 8.05 ppm (d, 2H); 11.7 ppm (s, 2H).

EXAMPLE 27

5-(4'Phenoxyphenyl)-5-[N-(2-hydroxyethyl)piperazinyl]barbituric Acid a) Preparation of N-[(4'-Phenoxybenzyl)thiocarbonyl]morpholine A mixture of (4'-phenoxyphenyl)methylketone (19.1 g), morpholine (20 ml) and sulphur (4.32 g) is refluxed for 24 hours, then it is extracted with diethyl ether. The organic phase is concentrated to dryness to give, after crystallization form a petroleum ether/ethyl acetate mixture 8:2 (600 ml), 12.2 g of the product, m.p. 75–77° C.

b) Preparation of (4'-phenoxyphenyl)acetic acid

A suspension of N-[(4'-phenoxybenzyl)thiocarbonyl]morpholine (1.725 g) in 87 ml of 10% potassium hydroxide is refluxed for 8 hours 30 minutes, then the reaction mixture is brought to room temperature and acidified with 1N hydrochloric acid. A white solid separates, which is stirred for 30 minutes and filtered. The solid is washed with water and dried under vacuum, to give 1.095 g of the product, m.p. 70–72° C.

c) Preparation of Ethyl (4'-Phenoxyphenyl)acetate

To a suspension of (4'-phenoxyphenyl)acetic acid (0.456 g) in 4 ml of ethanol is added para-toluensulfonic acid (0.076 g) and the resulting mixture is refluxed for 2 hours. The solvent is evaporated off, the residue is dissolved in diethyl ether and the organic phase is washed with saturated aqueous solution of sodium hydrogencarbonate and then with brine. The organic phase is dried over sodium sulfate and concentrated to dryness to give 0.458 g of the product as a brown oil.

d) Preparation of 5-(4'-Phenoxyphenyl)barbituric Acid

A soultion of sodium ethoxide (0.27 g) in 3 ml of anhydrous ethanol is added with 0.657 g of ethyl (4'-phenoxyphenyl)acetate dissolved in 5 ml of ethanol, then with urea (0.18 g). The reaction mixture is refluxed for 2 hours 30 minutes, then it is cooled to room temperature and the suspended solid is filtered. The solid is redissolved in 8 ml of water and the solution is acidified with 1 N hydrochloric acid. The solid which separates is recovered by filtration to give 0.165 g of the product, m.p. >240° C.

e) Preparation of 5-Bromo-5-(4'-phenoxyphenyl)barbituric Acid

To a suspension of 5-(4'-phenoxyphenyl)barbituric Acid (48 mg) in 0.23 ml of water, cooled at 0° C. and under stirring, are added 23 ml of 48% hydrobromic acid and successively 9 µl of bromine. After 2 hours at room temperature additional 9 µl of bromine are added and stirring is continued for 2 hours. The suspended solid is then filtered and washed with water, to give, after drying under vacuum at 60° C., 57 mg of the product, m.p. 125–127° C.

f) Preparation of the Title Compound

A solution of 5-Bromo-5-(4'-phenoxyphenyl)barbituric Acid (50 mg) in 0.2 ml of methanol is added dropwise with a solution of N-(2-hydroxyethyl)piperazine (52 mg) in 0.6 ml of methanol and the mixture is stirred for 2 hours. The white precipitate is recovered by filtration and dried under vacuum at 60° C. overnight. 42.6 mg of the product are obtained, m.p. >240° C. $^1$H-NMR in d6-DMSO: 2.2–2.45 ppm (m, 6H); 2.55 ppm (m, 4H); 3.45 ppm (m, 2H); 4.4 ppm (t, 1H); 6.9–7.7 ppm (m, 9H); 11.6 ppm (s, 2H).

EXAMPLE 28

5-Decyl-5-[N-(2-hydroxyethyl)piperazinyl]barbituric Acid a) Preparation of Diethyl Decylmalonate A solution of sodium (0.46 g) in 10 of anhydrous ethanol is added with 3.35 ml of diethyl malonate in 3 ml of ethanol and successively with a solution of decylbromide (4.15 ml) in 3 ml of ethanol. The reaction mixture is refluxed for 4 hours, then the precipitate is filtered off and the filtrate is concentrated to dryness. The residue is redissolved in a saturated aqueous solution of sodium hydrogensulfate and it is extracted with ethyl acetate. The organic extract is dried over sodium sulfate and the solvent is evaporated off. The resulting residue is used as such in the successive reaction.

b) Preparation of 5-Decylbarbituric Acid

To a solution of diethyl decylmalonate of step a) in 40 ml of ethanol are added 2.72 g of sodium ethoxide and then 1.8 g of urea. The reaction mixture is refluxed for 2 hours, then the precipitate is filtered and redissolved in 40 ml of water. The resulting aqueous solution is acidified with 6 N hydrochloric acid. The solid which separates is recovered by filtration and dried under vacuum at 40° C. overnight, to give 2.152 g of the product, m.p. 190° C.

c) Preparation of 5-Bromo-5-decylbarbituric Acid

To a suspension of 5-decylbarbituric Acid (0.537 g) in 2.9 ml of water are added under stirring at room temperature 0.29 ml of 48% hydrobromic acid. The mixture is cooled to 0° C. and 0.113 ml of bromine are dropped. The reaction mixture is stirred at room temperature for 1 hour 30 minutes, then the white precipitate is filtered and it is washed with water. The solid is partitioned between water and diethyl ether, the organic phase is separated, washed with brine and finally dried over sodium sulfate. By evaporation of the solvent under reduced pressure 0.62 g of the product are recovered.

d) Preparation of the Title Compound

To a solution of 5-Bromo-5-decylbarbituric Acid (0.619 g) in 1.3 ml of dimethylsulfoxide, kept under stirring at 0° C., a solution of 0.93 g of N-(2-hydroxyethyl)piperazine in 0.7 ml of dimethylsulfoxide is added dropwise, then the reaction is stirred at room temperature for 1 hour. The mixture is then cooled to 0° C. and added with 30 ml of water. A white solid separates, which is kept under stirring for 1 hour, then is filtered and dried under vacuum at 50° C. 0.309 g of the product are obtained, m.p. 181–182° C.

$^1$H-NMR in d6-DMSO: 0.85 ppm (t, 3H); 0.9–1.1 ppm (m, 2H); 1.15–1.4 ppm (m, 14H), 1.8–1.9 ppm (m, 2H); 2.2–2.45 ppm (m, 6H); 2.55 ppm (m, 4H); 3.45 ppm (m, 2H); 4.35 ppm (t, 1H), 11.55 ppm (s, 2H).

EXAMPLE 29

5-Hexdecyl-5-[N-(2-hydroxyethyl)piperazine] barbituric Acid

The title compound was prepared in an analogous manner like the compound of example 28.

EXAMPLE 30

5-Eicoxyl-5-[N-(2-hydroxyethyl)piperazine] barbituric Acid

The title compound was prepared in an analogous manner like the compound of example 28.

EXAMPLE 31

5-(4-Butoxyphenyl)-5-[4-(2-hydroxyphenyl) piperazinyl]barbituric Acid m.p. 184–185°

H-N.M.R. in d6-DMSO: 0.91 ppm (t, 3H); 1.4 ppm (m, 2H); 1.67 ppm (m, 2H), 2,36 ppm (m, 6H); 2.55 ppm (m, 4H; 3.44 ppm (q, 2H); 3.95 ppm (t, 2H); 4.37 ppm (t, 1H); 6.95 ppm (d, 2H); 7.28 ppm (d, 2H); 11.5 ppm (br. s, 2H).

The compound is prepared as described in Example 14. The only difference is in the preparation of the starting material ethyl 4-butoxyphenyl acetate, which can be prepared starting from 4-hydroxyphenylacetic acid by esterification with ethanol (see example 14a) and subsequenz alkylation of ethyl 4-hydroxyphenyl acetate with butyl bromide alkylation of ethyl 4-hydroxyphenyl acetate with butyl bromide, according to know methodologies.

EXAMPLE 32

The pathway of production as described in the specification and examplified in the previous examples the following compounds are synthesized. They are characterized by mass spectroscopy.

| 32.xx | Name | MW | exp. mass |
|---|---|---|---|
| 01 | N-(2,4,6-Trioxo-5-phenyl-hexahydro-pyrimidin-5-yl)-benzamide | 323.3 | 323 |
| 02 | 3-(3,4-Dimethoxy-phenyl)-N-(2,4,6-trioxo-5-phenyl-hexahydro-pyrimidin-5-yl)-acrylamide | 409.4 | 409 |
| 03 | 3-(3,4,5-Trimethoxy-phenyl)-N-(2.4,6-trioxo-5-phenyl-hexahydro-pyrimidin-5-yl)-acrylamide | 439.4 | 439 |
| 04 | 3-Phenyl-N-(2,4,6-trioxo-5-phenyl-hexahydro-pyrimidin-5-yl)-propionamide | 351.4 | 351 |
| 05 | 5-Phenyl-pentanoic acid (2,4,6-trioxo-5-phenyl-hexahydro-pyrimidin-5-yl)-amide | 379.4 | 379 |
| 06 | 2-(4-Nitro-phenyl)-N-(2,4,6-trioxo-5-phenyl-hexahydro-pyrimidin-5-yl)-acetamide | 382.3 | 382 |
| 07 | 3-Benzenesulfonyl-N-(2,4,6-trioxo-5-phenyl-hexahydro-pyrimidin-5-yl)-propionamide | 415.4 | 415 |
| 08 | 2-(4-Bromomethyl-phenyl)-N-(2,4,6-trioxo-5-phenyl-hexahydro-pyrimidin-5-yi)-acetamide | 430.3 | 429 |
| 09 | 2-Naphthalen-2-yl-N-(2,4,6-trioxo-5-phenyl-hexahydro-pyrimidin-5-yl)-acetamide | 387.4 | 387 |
| 10 | 2-(3-Chloro-phenyl)-N-(2,4,6-trioxo-5-phenyl-hexahydro-pyrimidin-5-yl)-acetamide | 371.8 | 371 |
| 11 | 3-(2-Methoxy-phenyl)-N-(2,4,6-trioxo-5-phenyl-hexahydro-pyrimidin-5-yl)-propionamide | 381.4 | 381 |
| 12 | 3-(4-Methoxy-phenyl)-N-2,4.6-trioxo-5-phenyl hexahydro-pyrimidin-5-yl)-propionamide | 381.4 | 381 |
| 13 | 2-(3-Bromo-phenyl)-N-(2,4.6-trixp-5-phenyl-hexahydro-pyrimidin-5-yl)-acetamide | 416.2 | 415 |
| 14 | 3-Phenyl-N-(2,4.6-trioxo-5-phenyl-hexahydro-pyrimidin-5-yl)-acrylamide | 349.3 | 349 |
| 15 | 4-Bromo-N-(2,4,6-trioxo-5-phenyl-hexahydro-pyrimidin-5 -yl)-benzamide | 402.2 | 401 |
| 16 | 3-Methyl-N-(2,4,6-trioxo-5-phenyl-hexahydro-pyrimidin-5-yl)-benzamide | 337.3 | 337 |
| 17 | 4-Methylsulfanyl-N-(2,4.6-trioxo-5-phenyl-hexahydro-pyrimidin-5-yl)-benzamide | 369.4 | 369 |

-continued

| 32.xx | Name | MW | exp. mass |
|---|---|---|---|
| 18 | 3-Chloro-N-(2,4,6-trioxo-5-phenyl-hexahydro-pyrimidin-5-yl)-benzamide | 357.8 | 357 |
| 19 | 4-Chloro-N-(2,4,6-trioxo-5-phenyl-hexahydro-pyrimidin-5-yl)-benzamide | 357.8 | 357 |
| 20 | 3,4-Dimethyl-N-(2,4,6-trioxo-5-phenyl-hexahydro-pyrimidin-5-yl)-benzamide | 351.4 | 351 |
| 21 | 3,5-Dimethyl-N-(2,4,6-trioxo-5-phenyl-hexahydro-pyrimidin-5-yl)-benzamide | 351.4 | 351 |
| 22 | 4-Ethoxy-N-(2,4,6-trioxo-5-phenyl-hexahydro-pyrimidin-5-yl)-benzamide | 367.4 | 367 |
| 23 | 4-Cyano-N-(2,4,6-trioxo-5-phenyl-hexahydro-pyrimidin-5-yl)-benzamide | 348.3 | 348 |
| 24 | 3-Methoxy-N-(2,4,6-trioxo-5-phenyl-hexahydro-pyrimidin 5-yl)-benzamide | 353.3 | 353 |
| 25 | 4-Methoxy-N-(2,4,6-trioxo-5-phenyl-hexahydro-pyrimidin-5-yl)-benzamide | 353.3 | 353 |
| 26 | 2-Methyl-N-(2,4,6-trioxo-5-phenyl-hexahydro-pyrimidin-5-yl)-benzamide | 337.3 | 337 |
| 27 | 2,4-Difluoro-N-(2,4,6-trioxo-5-phenyl-hexahydro-pyrimidin-5-yl)-benzamide | 359.3 | 359 |
| 28 | N-(2,4,6-Trioxo-5-phenyl-hexahydro-pyrimidin-5-yl)-isonicotinamide | 324.3 | 324 |
| 29 | Naphthalene-1-carboxylic acid (2,4,6-trioxo-5-phenyl-hexahydro-pyrimidin-5-yl)-amide | 373.4 | 373 |
| 30 | 1-(4-Fluoro-phenyl)-3-(2,4,6-trioxo-5-phenyl-hexahydro-pyrimidin-5-yl)-urea | 356.3 | 356 |
| 31 | 3-(4-Methoxy-phenyl)-N-(2,4,6-trioxo-5-phenyt-hexahydro-pyrimidin-5-yl)-acrylamide | 379.4 | 379 |
| 32 | 1-(3-Trifluoromethyl-phenyl)-3-(2,4,6-trioxo-5-phenyl-hexahydro-pyrimidin-5-yl)-urea | 406.3 | 406 |
| 33 | 3-(4-Chloro-phenyl)-N-(2,4,6-trioxo-5-phenyl-hexahydro-pyrimidin-5-yl)-acrylamide | 383.8 | 383 |
| 34 | 1-(2,4-Dichloro-phenyl)-3-(2,4,6-trioxo-5-phenyl-hexahydro-pyrimidin-5-yl)-urea | 407.2 | 406 |
| 35 | 1-(3,4-Dichloro-phenyl)-3-(2,4,6-trioxo-5-phenyl hexahydro-pyrimidin-5-yl)-urea | 407.2 | 406 |
| 36 | 1-(Chlor-phenyl)-3-(2,4,6-trioxo-5-phenyl-hcxahydro-pyrimidin-5-yl)-urea | 372.7 | 372 |
| 37 | 1-(4-Methoxy-phenyl)-3-(2,4,6-trioxo-5-phenyl hexahydro-pyrimidin-5-yl)-urea | 368.4 | 368 |
| 38 | 1-Phenyl-3-(2,4,6-trioxo-5-phenyl-hexahydro-pyrimidin-5-yl)-urea | 338.3 | 338 |
| 39 | Naphthalene-2-carboxylic acid (2,4,6-trioxo-5-phenyl hexahydro-pyrimidin-5-yl)-amide | 373.4 | 373 |
| 40 | 1H-Indole-5-carboxylic acid (2,4,6-trioxo-5-phenyl-hexahydro-pyrimidin-5-yl)-amide | 362.3 | 362 |
| 41 | N-(2,4,6-Trioxo-5-phenyl-hexahydro-pyrimidin-5-yl)-terephthalamide | 366.3 | 366 |
| 42 | 4-Sulfamoyl-N-(2,4,6-trioxo-5-phenyl-hexahydro-pyrimidin-5-yl)-benzamide | 402.4 | 402 |
| 43 | 4-Methyl-N-(2,4,6-trioxo-5-phenyl-hexahydro-pyrimidin 5 -yl)-benzamide | 337.3 | 337 |
| 44 | 4-Ethyl-N-(2,4,6-trioxo-5-phenyl-hexahydro-pyrimidin-5-yl)-benzamide | 351.4 | 351 |
| 45 | 4-Methyl-N-(2,4,6-trioxo-5-phenyl-hexahydro-pyrimidin 5-yl)-benzenesulfonamide | 373.4 | 373 |
| 46 | 4-Bromo-N-(2,4,6-trioxo-5-phenyl-hexahydro-pyrimidin-5-yl)-benzenesulfonamide | 438.3 | 437 |
| 47 | 2-Trifluoromethyl-N-(2,4,6-trioxo-5-phenyl-hexahydro-pyrimidin-5-yl)-benzenesulfonamide | 427.4 | 427 |
| 48 | 5-Phenyl-5-(4-phenyl-piperidin-1-yl)-pyrimidine-2,4,6-trione | 363.4 | 363 |
| 49 | 2,3-Dimethoxy-N-(2,4,6-trioxo-5-phenyl-hexahydro-pyrimidin-5-yl)-benzamide | 383.4 | 383 |
| 50 | 2,3-Dimethyl-N-(2,4,6-trioxo-5-phenyl-hexahydro-pyrimidin-5-yl)-benzamide | 351.4 | 351 |
| 51 | 4-Hydroxy-N-(2,4,6-trioxo-5-pheyl-hexahydro-pyrimidin-5-yl)-benzamide | 339.3 | 411 silyl. |
| 52 | 3,4-Dimethoxy-N-(2,4,6-trioxo-5-phenyl-hexahydro-pyrimidin-5-yl)-benzamide | 383.4 | 383 |
| 53 | 3-Dimethylamino-N-(2,4,6-trioxo-5-phenyl-hexahydro-pyrimidin-5-yl)-benzamide | 366.4 | 366 |
| 54 | 3-tert-Butyl-N-(2,4,6-trioxo-5-phenyl-hexahydro-pyrimidin-5-yl)-benzamide | 379.4 | 379 |
| 55 | 3,4-Dimethoxy-2-nitro-N-(2,4,6-trioxo-5-phenyl hexahydro-pyrimidin-5-yl)-benamide | 428.4 | 428 + FAB |

-continued

| 32.xx | Name | MW | exp. mass |
|---|---|---|---|
| 56 | 4-Butoxy-3-methoxy-N-(2,4,6-trioxo-5-phenyl-hexahydro-pyrimidin-5-yl)-benzamide | 425.4 | 425 + FAB |
| 57 | 2-Methyl-2,3-dihydro-benzofuran-7-carboxylic acid (2,4,6-trioxo-5-phenyl-hexahydro-pyrimidin-5-yl)-amide | 379.4 | 379 + FAB |
| 58 | 1H-Indole-4-carboxylic acid (2,4,6-trioxo-5-phenyl-hexahydro-pyrimidin-5-yl)-amide | 362.3 | 362 |
| 59 | 4-Methyl-3-sulfamoyl-N-(2,4,6-trioxo-5-phenyl-hexahydro-pyrimidin-5-yl)-benzamide | 416.4 | 416 |
| 60 | Acetic acid 6-methyl-2-nitro-3-(2,4,6-trioxo-5-phenyl-hexahydro-pyrimidin-5-ylcarbamoyl)-phenyl ester | 440.4 | 440 + FAB |
| 61 | Carbonic acid ethyl ester 2-methoxy-4-(2,4,6-trioxo-5-phenyl-hexahydro-pyrimidin-5-ylcarbamoyl)-phenyl ester | 441.4 | 441 + FAB |
| 62 | 2-Bromo-3-nitro-N-(2,4,6-trioxo-5-phenyl-hexahydro-pyrimidin-5-yl)-benzamide | 447.2 | 446 |
| 63 | "4-Chloro-sulfmoyl-N-(2,4,6-trioxo-5-phenyl-hexahydro-pyrimidin-5-yl)-benzamide e" | 436.8 | 436 |
| 65 | 3-tert-Butyl-2-hydroxy-N-(2,4,6-trioxo-5-phenyl-hexahydro-pyrimidin-5-yl)-benzamide | 395.4 | 395 |
| 66 | 4'-Benzyloxy-biphenyl-3-carboxylic acid (2,4,6-trioxo-5-phenyl-hexahydro-pyrimidein-5-yl)-amide | 505.5 | 505 + FAB |
| 67 | 3-Cyano-N-(2,4,6-trioxo-5-phenyl-hexahydro-pyrimidin-5-yl)-benzamide | 348.3 | 348 |
| 68 | 3-Bromo-N-(2,4,6-trioxo-5-phenyl-hexahydro-pyrimidin-5-yl)-benzamide | 402.2 | 401 |
| 69 | 3-Phenoxy-N-(2,4,6-trioxo-5-phenyl-hexhydro-pyrimdin-5-yl)-benzamide | 415.4 | 415 + FAB |
| 70 | 3-Benzoyl-N-2,4,6-trioxo-5-phenyl-hexahydro-pyrimidin-5-yl)-benzamide | 427.4 | 427 |
| 71 | 3-Trifluoromethyl-N-(2,4,6-trioxo-5-phenyl-hexahydro-pyrirmdin-5-yl)-benzamide | 391.3 | 391 |
| 72 | N-(2,4,6-Trioxo-5-phenyl-hexahydro-pyrimidin-5-yl)-isophthalamic acid methyl ester | 381.3 | 381 |
| 73 | 9H-Fluorene-1-carboxylic acid (2,4,6-trioxo-5-phenyl-hexahydro-pyrimidin-5-yl)-amide | 411.4 | 411 |
| 74 | 9-Oxo-9H-fluorene-1-carboxylic acid (2,4,6-trioxo-5-phenyl-hexadro-pyrimidin-5-yl)-amide | 425.4 | 425 |
| 75 | 5-Phenyl-5-(4-phenyl-piperazin-1-yl)-pyrimidine-2,4,6-trione | 364.4 | 364 |
| 76 | 5-Phenyl-5-[4-(2-trifluoromethyl-phenyl)-piperazin-l-yl]-pyrimidine-2,4,6-trione | 432.4 | 432 |
| 77 | 5-[4-(4-Nitro-phenyl)-piperazin-1-yl)-5-phenyl-pyrimidine-2,4,6-trione | 409.4 | 409 |
| 78 | 5-(4-Phenethyl-piperazin-1-yl)-5-phenyl-pyrimidine-2,4,6-trione | 392.5 | 392 |
| 79 | 5-[4-(3-Methoxy-phenyl)-piperazin-1-yl]-5-phenyl-pyrimidine-2,4,6-trione | 394.4 | 394 |
| 80 | 3-Acetylamino-N-(2,4,6-trioxo-5-phenyl-hexahydro-pyrimidin-5-yl)-benzamide | 380.4 | 380 |
| 81 | Acetic acid 3-(2,4,6-trioxo-5-phenyl-hexahydro-pyrimidin-5-ylcarbamoyl)-phenyl ester | 381.3 | 381 |
| 82 | 3-Ethoxy-N-(2,4,6-trioxo-5-phenyl-hexahydro-pyrimidin-5-yl)-benzamide | 367.4 | 367 |
| 83 | 5-Phenyl-5-(4-pyridin-4-yl-piperazin-1-yl)-pyrimidine-2,4,6-trione | 365.4 | 365 |
| 84 | 5-Phenyl-5-[4-(3-trifluoromethyl-phenyl)-piperazin-1-yl]-pyrimidine-2,4,6-trione | 432.4 | 432 |
| 85 | 5-[4-(4-Methoxy-phenyl)-piperazin-1-yl]-5-phenyl-pyrimidine-2,4,6-trione | 394.4 | 394 |
| 86 | 5-(4-Benzhydryl-piperazin-1-yl)-5-phenyl-pyrimidine-2,4,6-trione | 454.5 | 454 + FAB |
| 87 | 5-Phenyl-5-[4-(3-phenyl-allyl)-piperazin-1-yl]-pyrimidine-2,4,6-trione | 404.5 | 404 + FAB |
| 88 | 5-Phenyl-5-(2-pyrrolidin-1-yl-ethylamino)-pyrimidine-2,4,6-trione | 316.4 | 316 |
| 89 | 5-[2-(3H-Imidazol-4-yl)-ethylamin]-5-phenyl-pyrimidine-2,4,6-trione | 313.3 | 313 + FAB |

EXAMPLE 33

In order to determine the inhibition of MMPs, for example HNC, the catalytic domain (isolation and purification see for example Schnierer, S., Kleine, T., Gote, T., Hillemann, A., Knäuper, V., Tschesche, H., Biochem. Biophys. Res. Commun. (1993) 191, 319–326) is incubated with inhibitors having various concentrations. Subsequently, the initial reaction rate in the conversion of a standard substrate is measured in a manner analogous to Grams F. et al., FEBS 335 (1993) 76–80).

The results are evaluated by plotting the reciprocal reaction rate against the concentration of the inhibitor. The inhibition constant (Ki) is obtained as the negative section of the abscissis by the graphical method according to Dixon, M., Biochem. J. (1953) 55, 170–202.

The synthetic collagenase substrate is a heptapeptide which is coupled, at the C-terminus, with DNP (dinitrophenol). Said DNP residue quenches by steric hindrance the fluorescence of the adjacent tryptophane of the heptapeptide. After cleavage of a tripeptide which includes the DNP group, the tryptophane fluorescence increases. The proteolytic cleavage of the substrate therefore can be measured by the fluorescence value.

a) First Method

The assay was performed at 25° C. in a freshly prepared 50 mM Tris buffer (pH 8.0) treated with dithiozone to remove traces of heavy metals. 4 mM $CaCl_2$ was added and the buffer saturated wtih argon. Stock solutions of adamalysin II were prepared by centrifugation of the protein from an ammonium sulfate suspension and subsequent dissolution in the assay buffer. Stock solutions of collagenase were diluted with the assay buffer. Enzyme concentrations were determined by uv measurements ($\epsilon_{280}=2.8 \cdot 10^4$ M1 $cm^{-1}$, $\epsilon_{288}$: $2.2 \cdot 10^4$ $M^{-1}$ $cm^{-1}$) and the stock solutions were stored in the cold. This solution was diluted 1:100 to obtain the final 16 nM assay concentration. The fluorogenic substrate DNP-ProLeu-Gly-LeuTrp-Ala-D-Arg-$NH_2$ with a $K_m$ of 52 $\mu M$ was used at a concentration of 21.4 $\mu M$; for the $K_i$ determination a 12.8 $\mu M$ concentration has also been used. Substrate fluorescence was measured at an excitation and emission wavelength of $\lambda=320$ and 420 nm, respectively, on a spectrofluorimeter (Perkin Elmer, Model 650-40) equipped with a thermostated cell holder. Substrate hydrolysis was monitored for 10 min. immediately after adding the enzyme. All reactions were performed at least in triplicate. The $K_i$ values—of the inhibitors were calculated from the intersection point of the straight lines obtained by the plots of $v_o/v_i$ vs. [concentration of inhibitor], whereas $IC_{50}$ values were calculated from plots of $v_i/v_o$ [concentration of inhibitor] by non-linear regression with simple robust weighting.

b) Second Method

Assay buffer:

50 mM Tris/HCl pH 7.6 (Tris=Tris-(hydroxymethyl)-aminomethan)

100 mM NaCl/10 mM CaCl 2/5% MeOH (ff necessary)

Enzyme: 8 nM catalytic domain (Met80-Gly242) of human neutrophil collagenase

Substrate: 10 microM DNP-Pro-Leu-Gly-Leu-Trp-Ala-D-Arg-NH2

Total assay volume: 1 ml

A solution of the enzyme and inhibitor in assay buffer (25° C.) was prepared. The reaction was started directly by giving the substrate into the solution. The cleavage of the flourogenic substrate was followed by flourescence spectroscopy with an excitation and emision wavelength of 280 and 350 nm, respectively. The $IC_{50}$ value was calculated as the inhibitor concentration, which is necessary to decrease the velocity of the reaction to the half in comparison to the reaction without inhibitor.

Table 1 shows the $IC_{50}$ values found.

TABLE 1

IC50 Values of MMP-Inhibitor (MMP-8

| Compound | IC-50 [nM] |
| --- | --- |
| example 32.74 | 890 |
| preferred no. 120 | 150 |
| example 25 | 140 |
| example 23 | 110 |
| example 20 | 860 |
| example 32.77 | 160 |
| preferred no. 118 | 60 |
| example 28 | 320 |
| example 26 | 15 |

What is claimed is:

1. A compound of formula I

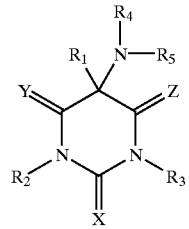

wherein:

X, Y and Z are each oxygen;

$R_1$ is phenyl which is unsubstituted or substituted by $C_1$–$C_4$ alkyl, $C_1$–$C_4$ alkoxy, hydroxyl, phenyl or phenoxy;

$R_2$ and $R_3$ are each hydrogen;

$R_4$ is hydrogen; and $R_5$ is an acyl residue CO—A—$R_6$, wherein A is a valence bond or a $C_1$–$C_9$ alkylene chain, and $R_6$ is selected from the group consisting of hydrogen, phenyl, naphthalinyl, indolyl, furyl, 9H-fluorenyl, 9-oxo-9H-fluorenyl, pyridinyl and styryl, wherein any of the rings designated above for $R_6$ may be substituted one, two or three times independently by a group selected from the group existing of $C_1$–$C_4$ alkyl, $C_1$–$C_4$ alkoxy, halogen, nitro, amino, mono- or dialkylamino, $SO_2NH_2$, $SCH_3$, CN, $CONH_2$, $CF_3$, phenoxy, benzoyl and $NHCOCH_3$, or $R_4$ and $R_5$, together with the nitrogen atom to which they are linked, form a piperidine or piperazine ring which is substituted by a group selected from the group consisting of hydroxyl, $C_1$–$C_4$ alkyl and $C_1$–$C_4$ alkoxy, wherein when $R_4$ and $R_5$ together with the nitrogen to which they are linked form a piperidine or a piperazine ring, $R_1$ is not a phenyl ring substituted by phenyl or phenoxy, or a pharmacologically acceptable salt or optically active form thereof.

2. A compound according to claim 1 wherein $R_1$ is phenyl.

3. A compound according to claim 1 wherein $R_6$ is phenyl or a substituted phenyl group.

4. A compound according to claim 1, wherein said compound comprises a piperidine and piperazine ring, selected from the group consisting of:

5-(1-[4-(2-hydroxyethyl)piperazinyl])-5-phenyl-barbituric Acid, 5-(1-[4-(2-hydroxyethyl)piperidinyl]-5-phenyl-barbituric Acid, 5-phenyl-5-(1-piperidinyl)barbituric Acid,
5-[1-(4-hydroxy)piperidinyl]-5-phenyl-barbituric Acid,
5-[1-(4-Methyl)-piperidinyl]-5-phenyl-barbituric Acid,
5-[1-(4-Methoxy)piperidinyl]-5-phenyl-barbituric Acid,
5-(4-Methoxyphenyl)-5-[N-(2-hydroxyethyl)piperazinyl] barbituric Acid,
5-[N-(2-hydroxyethyl)piperazinyl]-5-(4-hydroxyphenyl) barbituric Acid,
5-[N-(2-hydroxyethyl)piperazinyl]-5-(3-hydroxyphenyl) barbituric Acid,
5-[N-(2-hydroxyethyl)piperazinyl]-5-(4-Methylphenyl) barbituric Acid,
5-[4-(4-nitro-phenyl)-piperazin-1-yl]-5-phenyl-pyrimidine-2,4,6-trione.

5. A compound according to claim 1, wherein said compound comprises —NHR5=NH—CO—A—R$_6$ as benzamide, selected from the group consisting of:

N-(2,4,5-trioxo-5-phenyl-hexahydro-pyrimidin-5-yl)-benzamide,
4-Bromo-N-(2,4,6-trioxo-5-phenyl-hexahydro-pyrimidin-5-yl)-benzamide,
3-Methyl-N-(2,4,6-trioxo-5-phenyl-hexahydro-pyrimidin-5-yl)-benzamide,
4-Methylsulfanyl-N-(2,4,6-trioxo-5-phenyl-hexahydro-pyrimidin-5-yl)-benzamide,
3-chloro-N-(2,4,6-trioxo-5-phenyl-hexahydro-pyrimidin-5-yl)-benzamide,
4-chloro-N-(2,4,6-trioxo-5-phenyl-hexahydro-pyrimidin-5-yl)-benzamide,
3,4-dimethyl-N-(2,4,6-trioxo-5-phenyl-hexahydro-pyrimidin-5-yl)-benzamide,
3,5-dimethyl-N-(2,4,6-trioxo-5-phenyl-hexahydro-pyrimidin-5-yl)-benzamide,
4-ethoxy-N-(2,4,6-trioxo-5-phenyl-hexahydro-pyrimidin-5-yl)-benzamide,
4-cyano-N-(2,4,6-trioxo-5-phenyl-hexahydro-pyrimidin-5-yl)-benzamide,
3-Methoxy-N-(2,4,6-trioxo-5-phenyl-hexahydro-pyrimidin-5-yl)-benzamide,
4-Methoxy-N-(2,4,6-trioxo-5-phenyl-hexahydro-pyrimidin-5-yl)-benzamide,
2-Methyl-N-(2,4,6-trioxo-5-phenyl-hexahydro-pyrimidin-5-yl)benzamide,
2,4-difluoro-N-(2,4,6-trioxo-5-phenyl-hexahydro-pyrimidin-5-yl)-benzamide,
4-sulfamoyl-N-(2,4,6-trioxo-5-phenyl-hexahydro-pyrimidin-5-yl)-benzamide,
4-Methyl-N-(2,4,6-trioxo-5-phenyl-hexahydro-pyrimidin-5-yl)-benzamide,
4-ethyl-N-(2,4,6-trioxo-5-phenyl-hexahydro-pyrimidin-5-yl)-benzamide,
2,3-dimethoxy-N-(2,4,6-trioxo-5-phenyl-hexahydro-pyrimidin-5-yl)-benzamide,
2,3-dimethyl-N-(2,4,6-trioxo-5-phenyl-hexahydro-pyrimidin-5-yl)-benzamide,
4-hydroxy-N-(2,4,6-trioxo-5-phenyl-hexahydro-pyrimidin-5-yl)-benzamide,
3,4-dimethoxy-N-(2,4,6-trioxo-5-phenyl-hexahydro-pyrimidin-5-yl)-benzamide,
3-dimethylamino-N-(2,4,6-trioxo-5-phenyl-hexahydro-pyrimidin-5-yl)-benzamide,
3-tert-butyl-N-(2,4,6-trioxo-5-phenyl-hexahydro-pyrimidin-5-yl)-benzamide,
3,4-dimethoxy-2-nitro-N-(2,4,6-trioxo-5-phenyl-hexahydro-pyrimidin-5-yl)-benzamide,
4-butoxy-3-Methoxy-N-(2,4,6-trioxo-5-phenyl-hexahydro-pyrimidin-5-yl)-benzamide,
4-Methyl-3-sulfamoyl-N-(2,4,6-trioxo-5-phenyl-hexahydro-pyrimidin-5-yl)-benzamide,
2-Bromo-3-nitro-N-(2,4,6-trioxo-5-phenyl-hexahydro-pyrimidin-5-yl)-benzamide,
4-chloro-3-sulfamoyl-N-(2,4,6-trioxo-5-phenyl-hexahydro-pyrimidin-5-yl)-benzamide,
3-tert-butyl-2-hydroxy-N-(2,4,6-trioxo-5-phenyl-hexahydro-pyrimidin-5-yl)-benzamide,
3-cyano-N-(2,4,6-trioxo-5-phenyl-hexahydro-pyrimidin-5-yl)-benzamide,
3-Bromo-N-(2,4,6-trioxo-5-phenyl-hexahydro-pyrimidin-5-yl)-benzamide,
3-phenoxy-N-(2,4,6-trioxo-5-phenyl-hexahydro-pyrimidin-5-yl)-benzamide,
3-benzoyl-N-(2,4,6-trioxo-5-phenyl-hexahydro-pyrimidin-5-yl)-benzamide,
3-trifluoromethyl-N-(2,4,6-trioxo-5-phenyl-hexahydro-pyrimidin-5-yl)-benzamide,
3-acetylamino-N-(2,4,6-trioxo-5-phenyl-hexahydro-pyrimidin-5-yl)-benzamide, and
3-ethoxy-N-(2,4,6-trioxo-5-phenyl-hexahydro-pyrimidin-5-yl)-benzamide.

6. A compound according to claim 1, selected from the group consisting of:

3-(3,4-dimethoxy-phenyl)-N-(2,4,6-trioxo-5-phenyl-hexahydro-pyrimidin-5-yl)-acrylamide,
3-(3,4,5-trimethoxy-phenyl)-N-(2,4,6-trioxo-5-phenyl-hexahydro-pyrimidin-5-yl)-acrylamide,
3-phenyl-N-(2,4,6-trioxo-5-phenyl-hexahydro-pyrimidim-5-yl)-propionamide,
5-phenyl-pentanoic acid-(2,4,6-trioxo-5-phenyl-hexahydro-pyrimidin-5-yl)-amide,
2-(4-nitro-phenyl)-N-(2,4,6-trioxo-5-phenyl-hexahydro-pyrimidin-5-yl)-acetamide,
2-naphthalen-2-yl-N-(2,4,6-trioxo-5-phenyl-hexahydro-pyrimidin-5-yl)-acetamide,
2-(3-chloro-phenyl)-N-(2,4,6-trioxo-5-phenyl-hexahydro-pyrimidin-5-yl)-acetamide,
3-(2-Methoxy-phenyl)-N-(2,4,6-trioxo-5-phenyl-hexahydro-pyrimidin-5-yl)-propionamide,
3-(4-Methoxy-phenyl)-N-(2,4,6-trioxo-5-phenyl-hexahydro-pyrimidin-5-yl)-propionamide,
2-(3-Bromo-phenyl)-N-(2,4,6-trioxo-5-phenyl-hexahydro-pyrimidin-5-yl)-acetamide,
3-phenyl-N-(2,4,6-trioxo-5-phenyl-hexahydro-pyrimidin-5-yl)acrylamide,
N-(2,4,6-trioxo-5-phenyl-hexahydro-pyrimidin-5-yl)-isonicotinamide,
naphthalene-1-carboxylic acid-(2,4,6-trioxo-5-phenyl-hexahydro-pyrimidin-5-yl)-amide,
3-(4-Methoxy-phenyl)-N-(2,4,6-trioxo-5-phenyl-hexahydro-pyrimidin-5-yl)-acrylamide,
3-(4-chloro-phenyl)-N-(2,4,6-trioxo-5-phenyl-hexahydro-pyrimidin-5-yl)-acrylamide,
napthalene-2-carboxylic acid-(2,4,6-trioxo-5-phenyl-hexahydro-pyrimidin-5-yl)-amide, 1H-indole-5-carboxylic acid-(2,4,6-trioxo-5-phenyl-hexahydro-pyrimidin-5-yl)-amide, 9H-fluorene-1-carboxylic acid-(2,4,6-trioxo-5-phenyl-hexahydro-pyrimidin-5-yl)-amide, 9-oxo-9H-fluorene-1-carboxylic acid-(2,4,6-trioxo-5-phenyl-hexahydro-pyrimidin-5-yl)-amide.

7. A pharmaceutical composition comprising a compound according to claim 1, in combination with a pharmaceutically acceptable carrier.

* * * * *